(12) United States Patent
Houlihan et al.

(10) Patent No.: US 8,088,548 B2
(45) Date of Patent: Jan. 3, 2012

(54) BOTTOM ANTIREFLECTIVE COATING COMPOSITIONS

(75) Inventors: Francis M. Houlihan, Millington, NJ (US); Shinji Miyazaki, Shizuoka pref. (JP); Mark O. Neisser, Whitehouse Station, NJ (US); Alberto D. Dioses, Doylestown, PA (US); Joseph E. Oberlander, Phillipsburg, NJ (US)

(73) Assignee: AZ Electronic Materials USA Corp., Somerville, NJ (US)

( * ) Notice: Subject to any disclaimer, the term of this patent is extended or adjusted under 35 U.S.C. 154(b) by 301 days.

(21) Appl. No.: 11/876,793

(22) Filed: Oct. 23, 2007

(65) Prior Publication Data

US 2009/0104559 A1    Apr. 23, 2009

(51) Int. Cl.
G03F 7/11 (2006.01)
G03F 7/039 (2006.01)

(52) U.S. Cl. ............... 430/270.1; 430/288.1; 430/326; 430/271.1; 430/273.1; 522/15; 522/25

(58) Field of Classification Search ................. None
See application file for complete search history.

(56) References Cited

U.S. PATENT DOCUMENTS

| | | | |
|---|---|---|---|
| 3,523,795 A | 8/1970 | Ohkubo et al. | |
| 4,061,465 A | 12/1977 | Franklin et al. | |
| 4,197,174 A * | 4/1980 | Chang | 522/55 |
| 4,229,274 A | 10/1980 | Carlblom | |
| 4,388,450 A | 6/1983 | Crivello | |
| 4,491,628 A | 1/1985 | Ito et al. | |
| 4,845,265 A | 7/1989 | Lapin et al. | |
| 4,863,827 A | 9/1989 | Jain et al. | |
| 4,910,122 A | 3/1990 | Arnold et al. | |
| 5,069,997 A | 12/1991 | Schwalm et al. | |
| 5,114,826 A | 5/1992 | Kwong et al. | |
| 5,242,715 A * | 9/1993 | Schoen et al. | 427/386 |
| 5,286,867 A | 2/1994 | Lohaus et al. | |
| 5,338,641 A | 8/1994 | Pawlowski et al. | |
| 5,340,682 A | 8/1994 | Pawlowski et al. | |
| 5,350,660 A | 9/1994 | Urano et al. | |
| 5,354,643 A | 10/1994 | Cabrera et al. | |
| 5,362,608 A | 11/1994 | Flaim et al. | |
| 5,482,817 A | 1/1996 | Dichiara et al. | |
| 5,585,219 A | 12/1996 | Kaimoto et al. | |
| 5,635,333 A | 6/1997 | Petersen et al. | |
| 5,650,261 A | 7/1997 | Winkle | |
| 5,652,297 A | 7/1997 | McCulloch et al. | |
| 5,716,756 A | 2/1998 | Pawlowski et al. | |
| 5,731,386 A | 3/1998 | Thackeray et al. | |
| 5,837,420 A | 11/1998 | Aoai et al. | |
| 5,843,624 A | 12/1998 | Houlihan et al. | |
| 5,876,900 A | 3/1999 | Watanabe et al. | |
| 5,880,168 A | 3/1999 | Heinz et al. | |
| 5,880,169 A | 3/1999 | Osawa et al. | |
| 5,882,996 A | 3/1999 | Dai | |
| 5,886,102 A | 3/1999 | Sinta et al. | |
| 5,935,760 A | 8/1999 | Shan et al. | |
| 5,939,234 A | 8/1999 | Yamanaka et al. | |
| 5,939,235 A | 8/1999 | Kondo et al. | |
| 5,939,236 A | 8/1999 | Pavelchek et al. | |
| 5,972,560 A | 10/1999 | Kaneko | |
| 5,981,145 A | 11/1999 | Ding et al. | |
| 5,997,993 A | 12/1999 | Bi et al. | |
| 6,033,830 A | 3/2000 | Sinta et al. | |
| 6,054,254 A | 4/2000 | Sato et al. | |
| 6,080,530 A | 6/2000 | Shao et al. | |
| 6,103,445 A | 8/2000 | Willson et al. | |
| 6,110,653 A | 8/2000 | Holmes et al. | |
| 6,111,143 A | 8/2000 | Park et al. | |
| 6,114,085 A | 9/2000 | Padmanaban et al. | |
| 6,124,077 A | 9/2000 | Imai et al. | |
| 6,132,926 A | 10/2000 | Jung et al. | |
| 6,187,506 B1 | 2/2001 | Ding et al. | |
| 6,200,728 B1 * | 3/2001 | Cameron et al. | 430/270.1 |
| 6,207,342 B1 | 3/2001 | Takechi et al. | |
| 6,251,562 B1 | 6/2001 | Breyta et al. | |
| 6,319,651 B1 | 11/2001 | Holmes et al. | |
| 6,338,934 B1 | 1/2002 | Chen et al. | |
| 6,358,665 B1 | 3/2002 | Pawlowski et al. | |
| 6,395,450 B1 | 5/2002 | Park et al. | |
| 6,447,980 B1 | 9/2002 | Rahman et al. | |
| 6,455,230 B1 | 9/2002 | Damme et al. | |
| 6,723,488 B2 | 4/2004 | Kudo et al. | |
| 6,803,172 B2 | 10/2004 | Jung et al. | |
| 6,831,285 B2 | 12/2004 | Hol et al. | |
| 6,844,131 B2 | 1/2005 | Oberlander et al. | |
| 6,846,612 B2 | 1/2005 | Deshpande | |
| 6,866,984 B2 | 3/2005 | Baik et al. | |
| 7,070,914 B2 | 7/2006 | Neisser et al. | |
| 7,223,518 B2 | 5/2007 | Henderson et al. | |
| 7,265,431 B2 | 9/2007 | Sivakumar | |
| 7,358,408 B2 | 4/2008 | Rahman et al. | |

(Continued)

FOREIGN PATENT DOCUMENTS

DE    39 30 086 A1    3/1991

(Continued)

OTHER PUBLICATIONS

March, Jerry, "0-11 Hydroysis of Esters" from Advanced Organic Chemistry; Reactions, Mechanisms, and Structure, Second edition, year 1977, no month, pp. 349-353.* "Anion volumes database" obtaiend from http://www.warwick.ac.uk/fac/sci/Chemistry/thermochemistry/anion volumdatabase.htm on May 8, 2011 citing H.D.B.Jenks areticle with 1999 date as source of information., 14 pages.*
Form PCT/ISA/220, Form PCT/ISA/210, and Form PCT/ISA/237 for PCT/IB2008/002847 dated Oct. 6, 2009 which corresponds to U.S. Appl. No. 11/876,793.
English Language Abstract from JPO for JP 56-47440 A, printed Dec. 29, 2009.

(Continued)

*Primary Examiner* — Cynthia Hamilton
(74) *Attorney, Agent, or Firm* — Alan P. Kass; Sangya Jain

(57) ABSTRACT

Developable bottom antireflective coating compositions are provided.

16 Claims, No Drawings

U.S. PATENT DOCUMENTS

| | | | |
|---|---|---|---|
| 7,514,202 B2* | 4/2009 | Ohsawa et al. | 430/270.1 |
| 7,521,170 B2 | 4/2009 | Rahman et al. | |
| 7,521,483 B2 | 4/2009 | Davey et al. | |
| 7,541,134 B2 | 6/2009 | Iwabuchi et al. | |
| 7,678,528 B2 | 3/2010 | Rahman et al. | |
| 7,824,837 B2 | 11/2010 | Wu et al. | |
| 8,039,202 B2 | 10/2011 | Sui et al. | |
| 2002/0012880 A1 | 1/2002 | Imai et al. | |
| 2002/0045130 A1 | 4/2002 | Nitta et al. | |
| 2003/0129531 A1 | 7/2003 | Oberlander et al. | |
| 2003/0129547 A1* | 7/2003 | Neisser et al. | 430/322 |
| 2003/0162120 A1 | 8/2003 | Yoon et al. | |
| 2003/0215736 A1 | 11/2003 | Oberlander et al. | |
| 2004/0018451 A1 | 1/2004 | Choi | |
| 2004/0152009 A1 | 8/2004 | Yamaguchi et al. | |
| 2004/0229155 A1 | 11/2004 | Rahman et al. | |
| 2004/0248034 A1 | 12/2004 | Henderson et al. | |
| 2005/0053850 A1 | 3/2005 | Askebjer et al. | |
| 2005/0064326 A1* | 3/2005 | Yasunami et al. | 430/270.1 |
| 2005/0095532 A1* | 5/2005 | Kodama et al. | 430/270.1 |
| 2005/0214674 A1 | 9/2005 | Sui et al. | |
| 2005/0255410 A1 | 11/2005 | Guerrero et al. | |
| 2005/0271974 A1 | 12/2005 | Rahman et al. | |
| 2005/0277058 A1 | 12/2005 | Iwabuchi et al. | |
| 2005/0287816 A1 | 12/2005 | Blalock et al. | |
| 2006/0177774 A1 | 8/2006 | Abdallah et al. | |
| 2007/0015084 A1 | 1/2007 | Rahman et al. | |
| 2007/0031760 A1 | 2/2007 | Chang et al. | |
| 2007/0111138 A1 | 5/2007 | Rahman et al. | |
| 2007/0184648 A1 | 8/2007 | Yoon et al. | |
| 2007/0219368 A1 | 9/2007 | Iwabuchi et al. | |
| 2008/0008955 A1 | 1/2008 | Brodsky et al. | |
| 2008/0038666 A1 | 2/2008 | Wu et al. | |
| 2008/0090184 A1 | 4/2008 | Sui et al. | |
| 2008/0138744 A1 | 6/2008 | Hatanaka et al. | |
| 2009/0098490 A1 | 4/2009 | Pham et al. | |
| 2010/0119972 A1 | 5/2010 | Houlihan et al. | |
| 2011/0076626 A1 | 3/2011 | Padmanaban et al. | |
| 2011/0086312 A1 | 4/2011 | Dammel et al. | |

FOREIGN PATENT DOCUMENTS

| | | |
|---|---|---|
| DE | 39 30 087 A 1 | 3/1991 |
| EP | 0 794 458 A2 | 9/1997 |
| EP | 1 262 831 A2 | 12/2002 |
| JP | 56-47440 A | 4/1981 |
| JP | 6-295064 A | 10/1994 |
| JP | 2001-22057 A | 1/2001 |
| JP | 2004-31569 A | 1/2004 |
| JP | 2005-70154 A | 3/2005 |
| WO | WO 97/33198 A1 | 9/1997 |
| WO | WO 2005/093513 A2 | 10/2005 |
| WO | WO-2005/111724 A1 * | 11/2005 |

OTHER PUBLICATIONS

Database WPI Week 198125 Thomson Scientific, London, GB; AN 1981-44838D XP002546976 & JP 56 047440 A (Japan Synthetic Rubber Co Ltd) Apr. 30, 1981 & JP 56 047440 A (Japan Synthetic Rubber Co Ltd) Apr. 30, 1981.

Form PCT/ISa/206 for PCT/IB2008/002847, filed Jun. 16, 2009.

Nakano et al., "Positive-Type Photopolyimide Based on Vinyl Ether Crosslinking and De-Crosslinking", J. Photopolym.Sci. Technol., vol. 13, No. 5, pp. 715—pp. 718 (2000).

English Language Abstract from Derwent of JP 2001-22057 A, printed out May 5, 2010.

Form PCT/ISA/220, Form PCT/ISA/210 and Form PCT/IBSA/237 for PCT/IB2005/000773 dated Jul. 27, 2005 which corresponds to U.S. Appl. No. 10/808,884.

FormPCT/IB/326, Form PCT/IB/373 and Form PCT/IBSA/237 for PCT/IB2005/000773 dated Oct. 5, 2006 which corresponds to U.S. Appl. No. 10/808,884.

Office Action dated Jun. 24, 2008 from U.S. Appl. No. 11/876,332, which is a divisional of prior U.S. Appl. No. 10/808,884.

Office Action dated Jan. 27, 2009 from U.S. Appl. No. 11/876,332, which is a divisional of U.S. Appl. No. 10/808,884.

Office Action dated Mar. 13, 2009 from U.S. Appl. No. 11/876,332, which is a divisional of U.S. Appl. No. 10/808,884.

Office Action Oct. 30, 2009 from U.S. Appl. No. 11/876,332, which is a divisional of U.S. Appl. No. 10/808,884.

Office Action dated Apr. 30, 2009 from U.S. Appl. No. 11/877,891, which is a divisional of U.S. Appl. No. 10/808,884.

Office Action dated Oct. 29, 2009 from U.S. Appl. No. 11/877,891, which is a divisional of 10/808,884.

Invitation to Pay Additional Fees and, Where Applicable, Protest Fee (Form PCT/ISA/206) for PCT/IB2009/007451 dated Apr. 7, 2010, which corresponds to U.S. Appl. No. 12/269,072.

Form PCT/ISA/220, Form PCT/ISA/210, and Form PCT/ISA/237 for PCT/IB2009/007449 dated Feb. 10, 2010, which corresponds to U.S. Appl. No. 12/570,923.

Form PCT/ISA/220, Form PCT/ISA/210, and Form PCT/ISA/237 for PCT/IB2009/007456 dated Jan. 25, 2010, which corresponds to U.S. Appl. No. 12/576,622.

CRC Handbook of Chemistry & Physics, "Dissociation Constants of Organic Acids and Bases", CRC Press (1994-1995 75th Edition), pp. 8-45-pp. 8-55.

Ahn et al., "New Antireflective Coating Materials Containing a Novel Chromophore for KrF Laser Lithography", Journal of Photopolymer Science and Technology, vol. 14, No. 3, pp. 475-pp. 480 (2001).

Houlihan et al., "Chemically Amplified Resists: The Chemistry and Lithographic Characteristics of Nitrobenzyl Benzenesulfonate Derivatives", Journal of Photopolymer Science and Technology, vol. 1, No. 3, pp. 259-pp. 273 (1990).

Leonard V. Interrante, Chemistry of Materials, vol. 6, No. 10 (1994).

Lange's Handbook of Chemistry (15th Edition), Table 8.8 pKa Value of Organic Materials in Water at 25 degrees C Records 1428 and 1428, McGraw-Hill, www.knovel.com, 2 pages (1999).

Lee et al., "Performance of vinyl ether cross-linkers on resist for 193 nm lithography", SPIE, vol. 4690, pp. 541-548 (2002).

Jerry March, "Advanced Organic Chemistry: Reactions, Mechanisms, and Structure", Second Edition, McGraw-Hill Book Company, New York, NY, pp. 225-pp. 245 (1977).

Moon et al., Three-Component Photopolymers Based on Thermal Cross-Linking and Acidolytic De-Cross-Linking of Vinyl Ether Groups. Effects of Binder Polymers on Photopolymer Characteristics, *Chemical Materials*, vol. 6, pp. 1854-pp. 1860 (1994).

Moon et al., "Three-component photoresists based on thermal crosslinking and acidolytic cleavage", Polymer 41, pp. 4013-pp. 4019 (2000).

Moon et al., "Three-component Photoresists Containing Thermally Crosslinkable Generators", Polymer Engineering and Science vol. 41, No. 5, pp. 1248-pp. 1255 (May 2000)—XP000969783.

Noppakundilograt et al., "Visible Light-Sensitive Positive-Working Photopolymer Based on Poly(p-hydroxystyrene) and Vinyl Ether Crosslinker", Journal of Photopolymer Science and Technology vol. 13, No. 5, pp. 719-pp. 722 (2000).

Papadopoulos et al., "Dissociation of Salicylic Acid, 2,4-, 2,5-, and 2,6- Dihydroxybenzoic Acids in 1-Propanol—Water Mixtures at 25° C", Journal of Solution Chemistry, vol. 20, No. 3, pp. 293-pp. 300 (1991).

Schacht et al., "Acid Labile Cross-Linked Units: A Concept for Improved Positive Deep-UV Photoresists", American Chemical Society, pp. 78-pp. 94 (1998).

Schlegel et al., "Studies on the Acid Formation and Deprotection Reaction by Novel Sulfonates in a Chemical Amplification Positive Photoresist", Journal of Photopolymer & Science Technology, vol, 3, No. 3, pp. 281-pp. 287 (1990).

Shirai et al., "Photochemistry of Imino Sulfonate Compounds and Their Application to Chemically Amplified Resists", Journal of Photopolymer Science and Technology, vol. 3, No. 3, pp. 301-pp. 304 (1990).

White et al., "Synthesis and characterization of photodefinable polycarbonates for use as sacrificial materials in the fabrication of microfluid devices", SPIE vol. 4690, pp- 242-pp. 253 (2002).

Willson Research Group, University of Texas at Austin, "Aqueous Processable Positive and Negative Tone Photoresists", Apr. 18, 2001, available at http://willson.cm.utexas.edu/Research/Sub_Files/Water_Soluble/index.php (last visited May 6, 2010), with cover page.

Yamada et al., "The design and study of aqueous-processable positibe tone photoresists", SPIE vol. 3999, pp. 569-pp. 578 (2000).

Yamada et al., "Positive and Negative Tone Water Processable Photoresists: A Progress Report", SPIE vol. 3333, pp. 245-pp. 253 (2000).

Yamaoka et al., "Photochemical Dissociation of p-Nitrobenzyl Aromatic Sulfonate and Its Application to Chemical Amplification Resists", *Journal of Photopolymer Science and Technology*, vol. 3, No. 3, pp. 275-pp. 280 (1990).

Yamaoka et al., "Reaction of vinyl ethers and application of photoreactive process", Trends in Photochemistry & Photobiology, vol. 7, pp. 45-pp. 70 (2001).

Notice of Allowance and Fee(s) Due dated Jun. 16, 2010 from U.S. Appl. No. 11/876,332, which is a divisional of U.S. Appl. No. 10/808,884.

Notice of Allowance and Fee(s) Due dated May 27, 2010 from U.S. Appl. No. 11/877,891, which is a divisional of U.S. Appl. No. 10/808,884.

Notice of Allowance and Fee(s) Due dated Jul. 8, 2010 from U.S. Appl. No. 11/877,891, which is a divisional of U.S. Appl. No. 10/808,884.

Office Action dated Jul. 6, 2010 for U.S. Appl. No. 12/269,072.

Form PCT/ISA/220, Form PCT/ISA/210, and Form PCT/ISA/237 for PCT/IB2009/007451 dated Aug. 2, 2010, which corresponds to U.S. Appl. No. 12/269,072.

Moon et al., "Three-component photoresists based on thermal crosslinking and acidolytic cleavage", Polymer 41, pp. 4013-pp. 4019 (2000).

English Translation of Office Action dated Jul. 6, 2010 for Chinese Patent Application No. CN 200580011869.5, which corresponds to U.S. Appl. No. 10/808,884.

U.S. Appl. No. 12/269,072, filed Nov. 12, 2008, Houlihan et al.

U.S. Appl. No. 12/576,622, filed Oct. 9, 2009, Dammel et al.

U.S. Appl. No. 12/570,923, filed Sep. 30, 2009, Pedmanaban et al.

Notice of Allowance and Fee(s) Due dated Mar. 8, 2010 from U.S. Appl. No. 11/876,332, which is a divisional of U.S. Appl. No. 10/808,884.

English Translation of Notice of First Office Action dated Jul. 24, 2009 for Chinese Patent Application No. CN 200580011869.5, which corresponds to U.S. Appl. No. 10/808,884.

English Translation of Official Action mailed Oct. 12, 2010 for Japanese Patent Application No. 2007-504508, which corresponds to U.S. Appl. No. 10/808,884.

Office Action dated Feb. 1, 2011 from U.S. Appl. No. 11/877,891, which is a divisional of U.S. Appl. No. 10/808,884.

Office Action dated Sep. 22, 2010 from European Patent Office for European Application No. 08 843 074.9, which corresponds to U.S. Appl. No. 11/876,793.

Office Action dated Sep. 1, 2010 for U.S. Appl. No. 12/269,072.

Complete set of specification papers for U.S. Appl. No. 12/570,923, filed Sep. 30, 2009 with cover page.

Complete set of specification papers for U.S. Appl. No. 12/576,622, filed Oct. 9, 2009 with cover page.

Comm. pursuant to Article 94(3) EPC dated Feb. 17, 2011 from European Patent Office for European Patent Application No. 08 843 074.9, which corresponds to U.S. Appl. No. 11/876,793.

Office Action mail date Feb. 1, 2011 for U.S. Appl. No. 11/877,891.

Office Action dated Apr. 26, 2011 for U.S. Appl. No. 12/269,072.

Notice of Allowance and Fee(s) Due dated Jun. 15, 2011 from U.S. Appl. No. 11/877,891, which is a divisional of U.S. Appl. No. 10/808,884.

Advisory Action Before the Filing of an Appeal Brief dated Jul. 6, 2011 for U.S. Appl. No. 12/269,072.

Third Office Action dated Jul. 14, 2011 for Chinese Patent Application No. CN 200580011869.5, which corresponds to U.S. Appl. No. 10/808,884.

English Translation of Third Office Action dated Jul. 14, 2011 for Chinese Patent Application No. CN 200580011869.5, which corresponds to U.S. Appl. No. 10/808,884.

Eng. Trans. of Official Action mailed Sep. 13, 2011 from the JPO for Japanese Patent Application No. 2007-504508, which corresponds to U.S. Appl. No. 10/808,884.

Official Action received Aug. 17, 2011 from the KIPO for Korean Patent Application No. 10-2006-7022194, which corresponds to U.S. Appl. No. 10/808,884.

Eng. Trans. of Official Action received Aug. 17, 2011 from the KIPO for Korean Patent Application No. 10-2006-7022194, which corresponds to U.S. Appl. No. 10/808,884.

Office Action with Search Report from the Taiwan IPO received Sep. 13, 2011 for Taiwan Patent Application No. 094106806, which corresponds to U.S. Appl. No. 10/808,884.

Eng. Trans. of Office Action with Search Report from the Taiwan IPO received Sep. 13, 2011 for Taiwan Patent Application No. 094106806, which corresponds to U.S. Appl. No. 10/808,884.

* cited by examiner

BOTTOM ANTIREFLECTIVE COATING COMPOSITIONS

FIELD OF THE INVENTION

The present invention relates to aqueous developable coating compositions useful as coating layers in multilayer systems and new compounds for use therein.

BACKGROUND

In several industries (for example, the varnish, printing ink, paint, and lithography markets), multilayer systems are used in connection with a variety of substrates. In some instances, these systems contain acid-curable resins. Acid-curable resin compositions contain at least one component capable of acid-catalyzed polycondensation. These materials are familiar to those skilled in the art; they are produced industrially in large quantities with modifications to their material properties as appropriate for a great number of applications. Acid-curable resin compositions can contain, for example, alkyd resins, melamine resins, urea resins, guanamine resins, phenolic resins, polyester resins, (meth)acrylic resins, polyvinyl resins, vinyl ethers, vinyl esters, styrene/substituted styrene resins, polyimide resins, epoxide resins, urethane resins, and mixtures thereof. Examples of mixtures include, but are not limited to, melamine/(meth)acrylic resins, melamine/polyester resins, melamine/alkyd resins, vinyl ether/(meth)acrylic resins, vinyl ether/substituted styrene resins, and the like. One example where multilayer systems are used is the microlithography or photolithography industry.

Photoresist compositions are used in microlithography processes for making miniaturized electronic components such as in the fabrication of computer chips and integrated circuits. Generally, in these processes, a thin coating of a film of a photoresist composition is first applied to a substrate material, such as silicon wafers used for making integrated circuits. The coated substrate is then baked to evaporate any solvent in the photoresist composition and to fix the coating onto the substrate. The baked and coated surface of the substrate is next subjected to an image-wise exposure to radiation. The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the photoresist.

There are two types of photoresist compositions, negative-working and positive-working. When positive-working photoresist compositions are exposed image-wise to radiation, the areas of the photoresist composition exposed to the radiation become soluble in a developer solution while the unexposed areas of the photoresist coating remain relatively insoluble to such a solution. Thus, treatment of an exposed positive-working photoresist with a developer causes removal of the exposed areas of the photoresist coating and the formation of a positive image in the coating, thereby uncovering a desired portion of the underlying substrate surface on which the photoresist composition was deposited. In a negative-working photoresist the developer removes the portions that are not exposed.

The trend towards the miniaturization of semiconductor devices has led both to the use of new photoresists that are sensitive to lower and lower wavelengths of radiation, and also to the use of sophisticated multilevel systems to overcome difficulties associated with such miniaturization.

In these multilevel or multilayer systems, for example, the use of highly absorbing antireflective coatings in photolithography is a simpler approach to diminish the problems that result from back reflection of light from highly reflective substrates. A developable bottom antireflective coating is applied on the substrate and then a layer of photoresist is applied on top of the antireflective coating. The photoresist is exposed imagewise and developed. The developable bottom antireflective coating is also developable with the same aqueous alkaline developing solution as that used to typically develop the photoresist. Additionally, barrier coatings or top antireflective coatings or immersion protection coatings are also used in multilayer systems.

Often times, the formulations used in the coatings industries, are baked at temperatures above room temperature. The baking temperatures can vary, depending upon the type of coating applied and its desired use. In some instances, having a coating which contains a thermal acid generator with a low decomposition temperature, which in turn relates to a low baking temperature, is beneficial.

SUMMARY OF THE INVENTION

A multilayer system is disclosed having at least a first layer and a second layer, wherein the first layer contains a photoacid generator that is substantially insoluble in a solvent of the second layer is disclosed. The multilayer system can optionally have a third layer present under the first layer where the photoacid generator of the first layer is substantially insoluble in a solvent of the third layer.

Also, a positive bottom photoimageable antireflective coating composition which is capable of being developed with an aqueous alkali developer and which is coated below a positive photoresist, wherein the antireflective coating composition comprises a polymer, and a photoacid generator comprising a cation having a volume of less than or equal to about 450 cubic angstroms and an anion, where the photoacid generator is substantially insoluble in a solvent of the photoresist is disclosed.

Also disclosed is a negative bottom photoimageable antireflective coating composition which is capable of being developed with an aqueous alkali developer and which is coated below a negative photoresist, wherein the antireflective coating composition comprises a photoacid generator comprising a cation having a volume of less than or equal to about 450 cubic angstroms and an anion, a crosslinking agent and a polymer. The negative bottom photoimageable antireflective coating can comprise a photoacid generator comprising a cation having a volume of less than or equal to about 450 cubic angstroms and an anion, a crosslinking agent and an alkali soluble polymer comprising at least one unit with an absorbing chromophore; or the negative bottom photoimageable antireflective coating can comprise a photoacid generator comprising a cation having a volume of less than or equal to about 450 cubic angstroms and an anion, a crosslinking agent, a dye and an alkali soluble polymer, the absorbing chromophore present within the polymer or as an additive in the composition; or the negative bottom photoimageable antireflective coating composition consists of a photoacid generator comprising a cation having a volume of less than or equal to about 450 cubic angstroms and an anion and a polymer that changes polarity or functionality in the presence of the photolyzed photoactive compound such that its solubility in aqueous base is changed from soluble to insoluble after exposure, the absorbance being intrinsic to the polymer or due to an added dye.

Also disclosed are mono functionalized ammonium salts of certain dicarboxylic acids, a compound of formula (I), that makes very good thermal acid generators for use in heat activated acid-curable resin compositions, which are useful in the multilayer systems as described herein. The heat activated acid-curable resin compositions can be those which form irreversible crosslinked systems, for example paints and non-developable antireflective coatings (both carbon based and silicon based), for example, paints and coatings, as well as those which form reversible crosslinked systems, for example developable antireflective coatings and photoresist coatings.

(I)

where Y is selected from a direct bond and a connecting group; and A is an unsubstituted or substituted amine compound. Also disclosed is a heat activated acid-curable resin composition comprising at least one resin capable of acid-catalyzed polycondensation and a compound of formula (I). The connecting group Y can be selected from $C_1$-$C_8$ unsubstituted or substituted alkylene chain optionally containing one or more hetero atoms (for example, O, S, SO, $SO_2$, —C(=O)—, —C(=O)O—, —O—C(=O)—O—, —OC(=O)—), $C_3$-$C_8$ unsubstituted or substituted cycloalkylene, $C_2$-$C_8$ unsubstituted or substituted alkenylene, and $C_6$-$C_{12}$ unsubstituted or substituted arylene. Furthermore, it can be $C_1$-$C_8$ unsubstituted or substituted alkylene chain optionally containing one or more hetero atoms, even still, $C_1$-$C_8$ unsubstituted or substituted alkylene chain optionally containing one or more O atoms, and yet even still $C_1$-$C_8$ unsubstituted or substituted alkylene chain, $C_1$-$C_3$ unsubstituted or substituted alkylene chain, or even $C_1$-$C_3$ alkylene chain substituted with hydroxyl and/or alkyl.

The amine compound can be selected such that it volatizes at a temperature at which compositions which contain the compound of formula (I) are thermally cured. Examples of the amine compound include a compound selected from the group consisting of

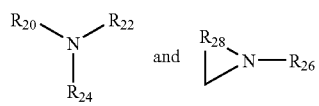

where each of $R_{20}$, $R_{22}$, $R_{24}$, and $R_{26}$ are individually selected from hydrogen, unsubstituted or substituted alkyl, unsubstituted or substituted cycloalkyl, unsubstituted or substituted monocyclic or polycyclic aryl, and unsubstituted or substituted aralkyl; and $R_{28}$ is selected from $C_3$-$C_7$ unsubstituted or substituted alkylene or $R_{28}$ together with the atoms to which it is bound forms a $C_6$-$C_{12}$ unsubstituted or substituted monocyclic or polycyclic aryl. Further examples include ammonia, unsubstituted and substituted trialkylamines, unsubstituted and substituted dialkylamines, and unsubstituted and substituted monoalkylamines, unsubstituted and substituted tricycloalkylamines, unsubstituted and substituted dicycloalkylamines, and unsubstituted and substituted monocycloalkylamines, unsubstituted and substituted monocylcoalkyldialkylamines, unsubstituted and substituted dicycloalkylmonoalkylamines, unsubstituted and substituted monoaryldialkylamines, unsubstituted and substituted diarylmonoalkylamines, unsubstituted and substituted triarylamines, unsubstituted and substituted diarylamines, and unsubstituted and substituted monoarylamines, unsubstituted and substituted triaralkylamines, unsubstituted and substituted diaralkylamines, and unsubstituted and substituted monoaralkylamines, unsubstituted and substituted monoaralkyldialkylamines, unsubstituted and substituted diaralkylmonoalkylamines, unsubstituted and substituted monoarylmonoalkylamines, unsubstituted and substituted monoarallylmonoalkylamines, unsubstituted and substituted monocycloalkylmonoalkylamines, and unsubstituted and substituted monoarylmonocycloalkylamines and the like, etc. Further examples include trimethylamine, dimethylethylamine, dimethylpropylamine, dimethylbutylamine, methyldiethylamine, methyldipropylamine, methyldibutylamine, methylethylpropylamine, methylethylbutylamine, methylpropylbutylamine, triethylamine, ethyldipropylamine, ethyldibutylamine, diethylpropylamine, diethylbutylamine, ethylpropylbutylamine, tripropylamine, dipropylbutylamine, propyldibutylamine, tributylamine, pyrrolidine, piperidine, piperazine, cyclohexyl amine, and the like.

Also disclosed is a coated substrate comprising a substrate having thereon; a layer of the antireflective coating composition of the present invention; and a layer of a photoresist composition above the antireflective coating composition. Also disclosed is a process for forming an image comprising a) forming a coating of the bottom photoimageable antireflective coating composition of the present invention on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

The coating composition of the present invention can also be used as a barrier layer when the resin system that is used is transparent (not absorbing) at the wavelength where the composition would be used. When used as a barrier layer, it is placed between a photoresist and a substrate to prevent contamination and defects (e.g., scumming, footing, etc) from occurring.

DETAILED DESCRIPTION OF THE INVENTION

A multilayer system is disclosed having at least a first layer and a second layer, wherein the first layer contains a photoacid generator that is substantially insoluble in a solvent of the second layer is disclosed. The multilayer system can optionally have a third layer present under the first layer where the photoacid generator of the first layer is substantially insoluble in a solvent of the third layer.

Also, a positive bottom photoimageable antireflective coating composition which is capable of being developed with an aqueous alkali developer and which is coated below a positive photoresist, wherein the antireflective coating composition comprises a polymer, and a photoacid generator comprising a cation having a volume of less than or equal to about 450 cubic angstroms and an anion, where the photoacid generator is substantially insoluble in a solvent of the photoresist is disclosed.

Also disclosed is a negative bottom photoimageable antireflective coating composition which is capable of being developed with an aqueous alkali developer and which is coated below a negative photoresist, wherein the antireflective coating composition comprises a photoacid generator comprising a cation having a volume of less than or equal to about 450 cubic angstroms and an anion, a crosslinking agent and a polymer where the photoacid generator is substantially insoluble in a solvent of the photoresist. The negative bottom photoimageable antireflective coating can comprise a photoacid generator comprising a cation having a volume of less than or equal to about 450 cubic angstroms and an anion, a crosslinking agent and an alkali soluble polymer comprising at least one unit with an absorbing chromophore where the photoacid generator is substantially insoluble in a solvent of the photoresist; or the negative bottom photoimageable antireflective coating can comprise a photoacid generator comprising a cation having a volume of less than or equal to about 450 cubic angstroms and an anion, a crosslinking agent, a dye and an alkali soluble polymer, the dye present within the polymer or as an additive in the composition, where the photoacid generator is substantially insoluble in a solvent of the photoresist; or the negative bottom photoimageable antireflective coating composition comprises a photoacid generator comprising a cation having a volume of less than or equal to about 450 cubic angstroms and an anion and a polymer that changes polarity or functionality in the presence of the photolyzed photoactive compound such that its solubility in aqueous base is changed from soluble to insoluble after exposure, the absorbance being intrinsic to the polymer or due to an added dye, where the photoacid generator is substantially insoluble in a solvent of the photoresist.

Also disclosed are mono functionalized ammonium salts of certain dicarboxylic acids, a compound of formula (I), that makes very good thermal acid generators for use in heat activated acid-curable resin compositions, which are useful in the multilayer systems as described herein. The heat activated acid-curable resin compositions can be those which form irreversible crosslinked systems, for example paints and non-developable antireflective coatings (both carbon based and silicon based), for example, paints and coatings, as well as those which form reversible crosslinked systems, for example developable antireflective coatings and photoresist coatings.

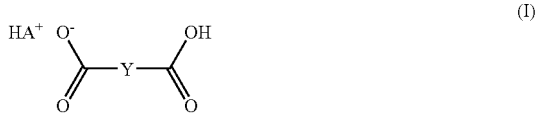

(I)

where Y is selected from a direct bond and a connecting group; and A is an unsubstituted or substituted amine compound. Also disclosed is a heat activated acid-curable resin composition comprising at least one resin capable of acid-catalyzed polycondensation and a compound of formula (I). The connecting group Y can be selected from $C_1$-$C_8$ unsubstituted or substituted alkylene chain optionally containing one or more hetero atoms (for example, O, S, SO, $SO_2$, —C(=O)—, —C(=O)O—, —O—C(=O)—O—, —OC(=O)—), $C_3$-$C_8$ unsubstituted or substituted cycloalkylene, $C_2$-$C_8$ unsubstituted or substituted alkenylene, and $C_6$-$C_{12}$ unsubstituted or substituted arylene. Furthermore, it can be $C_1$-$C_8$ unsubstituted or substituted alkylene chain optionally containing one or more hetero atoms, even still, $C_1$-$C_8$ unsubstituted or substituted alkylene chain optionally containing one or more O atoms, and yet even still $C_1$-$C_8$ unsubstituted or substituted alkylene chain, $C_1$-$C_3$ unsubstituted or substituted alkylene chain, or even $C_1$-$C_3$ alkylene chain substituted with hydroxyl and/or alkyl.

The amine compound can be selected such that it volatizes at a temperature at which compositions which contain the compound of formula (I) are thermally cured. Examples of the amine compound include a compound selected from the group consisting of

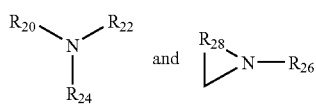

where each of $R_{20}$, $R_{22}$, $R_{24}$, and $R_{26}$ are individually selected from hydrogen, unsubstituted or substituted alkyl, unsubstituted or substituted cycloalkyl, unsubstituted or substituted monocyclic or polycyclic aryl, and unsubstituted or substituted aralkyl; and $R_{28}$ is selected from $C_3$-$C_7$ unsubstituted or substituted alkylene or $R_{28}$ together with the atoms to which it is bound forms a $C_6$-$C_{12}$ unsubstituted or substituted monocyclic or polycyclic aryl. Further examples include ammonia, unsubstituted and substituted trialkylamines, unsubstituted and substituted dialkylamines, and unsubstituted and substituted monoalkylamines, unsubstituted and substituted tricycloalkylamines, unsubstituted and substituted dicycloalkylamines, and unsubstituted and substituted monocycloalkylamines, unsubstituted and substituted monocylcoalkyldialkylamines, unsubstituted and substituted dicycloalkylmonoalkylamines, unsubstituted and substituted monoaryldialkylamines, unsubstituted and substituted diarylmonoalkylamines, unsubstituted and substituted triarylamines, unsubstituted and substituted diarylamines, and unsubstituted and substituted monoarylamines, unsubstituted and substituted triaralkylamines, unsubstituted and substituted diaralkylamines, and unsubstituted and substituted monoaralkylamines, unsubstituted and substituted monoaralkyldialkylamines, unsubstituted and substituted diaralkylmonoalkylamines, unsubstituted and substituted monoarylmonoalkylamines, unsubstituted and substituted monoarallylmonoalkylamines, unsubstituted and substituted monocycloalkylmonoalkylamines, and unsubstituted and substituted monoarylmonocycloalkylamines and the like, etc. Further examples include trimethylamine, dimethylethylamine, dimethylpropylamine, dimethylbutylamine, methyldiethylamine, methyldipropylamine, methyldibutylamine, methylethylpropylamine, methylethylbutylamine, methylpropylbutylamine, triethylamine, ethyldipropylamine, ethyldibutylamine, diethylpropylamine, diethylbutylamine, ethylpropylbutylamine, tripropylamine, dipropylbutylamine, propyldibutylamine, tributylamine, pyrrolidine, piperidine, piperazine, cyclohexyl amine, and the like.

Also disclosed is a coated substrate comprising a substrate having thereon; a layer of the antireflective coating composition of the present invention; and a layer of a photoresist composition above the antireflective coating composition. Also disclosed is a process for forming an image comprising a) forming a coating of the bottom photoimageable antireflective coating composition of the present invention on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

The coating composition of the present invention can also be used as a barrier layer when the resin system that is used is transparent (not absorbing) at the wavelength where the composition would be used. When used as a barrier layer, it is placed between a photoresist and a substrate to prevent contamination and defects (e.g., scumming, footing, etc) from occurring.

As mentioned above, there are two types of photoresists, positive and negative, and as such, the complementary bottom photoimageable antireflective coating compositions are also of two types, positive bottom photoimageable antireflective coating compositions and negative bottom photoimageable antireflective coating compositions.

Regarding the positive bottom photoimageable antireflective coating compositions, a polymer useful in positive bottom photoimageable antireflective coating compositions include a polymer selected from the group of (i) a polymer comprising at least one recurring unit with an acid labile group; (ii) a polymer comprising at least one recurring unit with an acid labile group and at least one recurring unit with an absorbing chromophore or (iii) a polymer comprising at least one recurring unit with a hydroxyl and/or a carboxyl group and at least one recurring unit with an absorbing chromophore.

One polymer useful in positive bottom photoimageable antireflective coating compositions is (i) a polymer which comprises at least one unit with an acid labile group. One function of the polymer is to provide a good coating quality and another is to enable the antireflective coating to change solubility from exposure to development. The acid labile groups in the polymer provide the necessary solubility change. The polymer without the acid labile group is soluble in an aqueous alkaline solution, but when protected with an acid labile group becomes insoluble. Examples of monomers that impart alkali solubility are acrylic acid, methacrylic acid, vinyl alcohol, hydroxystyrenes, vinyl monomers containing 1,1',2,2',3,3'-hexafluoro-2-propanol and sulfonamides (e.g., 2-trifluoromethanesulfonylaminoethyl methacrylate and 2-sulfonylamino-2,2-difluoroethylmethacrylate), although any group that makes the polymer alkali soluble may be used. The hydrophilic functionalities can be protected with acid labile groups such as alkyl, cycloalkyl, substituted cycloalkyl, oxocyclohexyl, cyclic lactone, benzyl, silyl, alkyl silyl, substituted benzyl, alkoxy alkyl such as ethoxy ethyl or methoxy ethoxy ethyl, acetoxyalkoxy alkyl such as acetoxy ethoxy ethyl, tetrahydrofuranyl, menthyl, tetrahydropyranyl and mevalonic lactone. Examples acid labile groups include, but are not limited to, t-butoxycarbonyl, tricyclo(5.3.2.0)decanyl, 2-methyl-2-adamantyl, isobornyl, norbornyl, adamantyloxyethoxy ethyl, menthyl, tertiary butyl, tetrahydropyrany, 3-oxocyclohexyl, 3-hydroxy-1-adamantyl, 2-methyl-2-adamantyl, beta-(gamma-butyrolactonyl), and mevalonic lactone. Some of the monomers are vinyl compounds with the above mentioned labile groups. The acid labile group that can be cleaved with an acid may be attached to the polymer, which in the presence of an acid gives an alkali soluble polymer. The protected monomers may be polymerized to give homopolymers or with other unprotected monomers as required. Alternatively, an alkali soluble homopolymer or copolymer may be reacted with a compound, or compounds, which provide the acid labile group. When this polymer is used to form the antireflective coating composition, a dye as well as a photo-acid generator will typically be present in the composition. This dye may be monomeric, polymeric or mixtures of both.

Examples of absorbing groups that may be contained in an additive absorbing compound are substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Absorbing polymeric dyes that may be used are polymers of the absorbing moieties listed above, where the polymer backbone may be polyesters, polyimides, polysulfones and polycarbonates. Some dyes are copolymers of hydroxystyrene and methyl methacrylate and azo polymeric and monomeric dyes. Examples of dyes are monomers or polymers of the list of chromophores mentioned below.

Another polymer useful in positive bottom photoimageable antireflective coating compositions is (ii) a polymer comprising at least one unit with an acid labile group and at least one unit with an absorbing chromophore. A skilled artisan will appreciate which chromophores are useful at the exposure wavelength of interest. Examples of an absorbing chromophore are hydrocarbon aromatic moieties and heterocyclic aromatic moieties with from one to four separate or fused rings, where there are 3 to 10 atoms in each ring. Examples of monomers with absorbing chromophores that can be polymerized with the monomers containing the acid labile groups are vinyl compounds containing substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Other chromophores are described in U.S. Pat. No. 6,114,085, and in U.S. Pat Nos. 5,652,297, 5,763,135, 5,981,145, 6,187,506, 5,939,236, and 5,935,760, which may also be used, and are incorporated herein by reference. Examples of the monomers include, for example, styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy)ethyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl)maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate and equivalent structures. Any chromphore that absorbs at the appropriate exposure wavelength may be used alone or in combination with other chromophores. Thus a polymer may be synthesized by polymerizing monomers that contain an acid labile group with monomers that contain an absorbing chromophore. Alternatively, the alkali soluble polymer may be reacted with compounds that provide the acid labile group and compounds that provide the absorbing chromophore. The mole % of the acid labile unit in the final polymer can range from 5 to 95, and the mole % of the absorbing chromophore unit in the final polymer can range from 5 to 95. Also the acid labile group is attached to the absorbing chromphore or that the chromophore is attached to the acid labile group, for example the monomers may be $CH_2=CHX-Ar-(CO)_nO-R$ (n=0-1), CH₂=CHX—Ar—OC(O)O—R, (CH)=CHX—Ar—C(CF₃)₂O—R, CH₂=CHX—Ar—C(CF₃)₂O(CO)O—R, CH₂=CHX—Ar—C(CF₃)₂(COOR), CH₂=CHX—C(O)O—Ar—OC(O)—R, CH₂=CHX—CON(X)—Ar—O—R, and vinyl compounds containing —(CO)O—R—Ar, —OC(O)O—R—Ar, —C(CF₃)₂O—R—Ar, —C(CF₃)₂O(CO)O—R—Ar, C(CF₃)₂(COOR—Ar), where X is H or alkyl, Ar is substituted and unsubstituted phenyl such as phenyl or benzyl, substituted and unsubstituted anthracyl such as anthracylmethyl, substituted and unsubstituted phenanthryl, substituted and unsubstituted naphthyl, substituted and unsubstituted heterocyclic aromatic rings containing heteroatoms such as oxygen, nitrogen, sulfur, or combinations thereof, such as pyrrolidinyl, pyranyl, piperidinyl, acridinyl, quinolinyl, and R is alkyl, cycloalkyl, substituted cycloalkyl, oxocyclohexyl, cyclic lactone, benzyl, substituted benzyl, alkoxy alkyl, such as ethoxy ethyl or methoxy ethoxy ethyl, acetoxy ethoxy ethyl, tetrahydrofuranyl, menthyl, tetrahydropyranyl, mevalonic lactone. Examples of R include, for example, t-butoxycarbonyl tricyclo(5.3.2.0) decanyl, 2-methyl-2-adamantol, isobornyl, norbornyl, adamantyloxyethoxy ethyl, menthyl, tertiary butyl, tetrahydropyranyl, 3-oxocyclohexyl.

In addition to the unit containing the acid labile group and the absorbing chromphore, the polymer may contain other nonabsorbing monomeric units, such units may provide other desirable properties. A skilled artisan will appreciate which nonabsorbing monomeric units can be useful at the exposure wavelength of interest. Examples of the third monomer include —CR₁R₂—CR₃R₄—, where R₁ to R₄ are independently H, (C₁-C₁₀) alkyl, (C₁-C₁₀) alkoxy, nitro, halide, cyano, alkylaryl, alkenyl, dicyanovinyl, SO₂CF₃, COOZ, SO₃Z, COZ, OZ, NZ₂, SZ, SO₂Z, NHCOZ, SO₂NZ₂, where Z is H, or (C₁-C₁₀) alkyl, hydroxy (C₁-C₁₀) alkyl, (C₁-C₁₀) alkylOCOCH₂COCH₃, or R₂ and R₄ combine to form a cyclic group such as anhydride, pyridine, or pyrollidone, or R₁ to R₃ are independently H, (C₁-C₁₀) alkyl, (C₁-C₁₀) alkoxy and R₄ is a hydrophilic group. Examples of the hydrophilic group, are given here but are not limited to these: O(CH₂)₂OH, O(CH₂)₂₀(CH₂)OH, (CH₂)ₙOH (where n=0-4), COO(C₁-C₄) alkyl, COOX and SO₃X (where X is H, ammonium, alkyl ammonium). Other hydrophilic vinyl monomers that can be used to form the polymer are acrylic acid, methacrylic acid, vinyl alcohol, maleic anhydride, maleic acid, maleimide, N-methyl maleimide, N-hydroxymethyl acrylamide and N-vinyl pyrrolidinone. Other monomers may be methyl methacrylate, butyl methacrylate, hydroxyethyl methacrylate and hydroxypropyl methacrylate. Monomeric units containing acid labile groups may also be used, such as hydroxystyrene, vinyl alcohol, (meth)acrylic acid capped with acid labile groups. Examples of acid labile groups, without limitation, are secondary and tertiary alkyls (up to 20 carbon atoms) with at least one β hydrogen, acetals and ketals, trimethylsilyl, and β-trimethylsilyl substituted alkyls. Representative examples of acid labile groups are tert-butyl, tert-pentyl, isobornyl, 1-alkylcyclohexyl, 1-alkylcyclopentyl, cyclohexyl, 2-alkyl-2-adamantyl, 2-alkyl-2-norbornyl. Other examples of acid labile groups are tetrahydrofuranyl, tetrahydropyranyl, substituted or unsubstituted methoxycarbonyl, β-trialkylsilylalkyl groups (e.g. CH₂—CH₂Si(CH₃)₃, CH(—CH₂Si(CH₃)₃)₂, CH₂—CH(Si(CH₃)₃)₂) and the like.

Examples of monomers containing acid labile groups that can be used in the polymers include methacrylate ester of methyladamantane, methacrylate ester of mevalonic lactone, 3-hydroxy-1-adamantyl methacrylate, methacrylate ester of beta-hydroxy-gamma-butyrolactone, t-butyl norbornyl carboxylate, t-butyl methyl adamantyl methacrylate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris(trimethylsilyl)silyl ethyl ester of methyl methacrylate.

The monomers containing an absorbing chromophore include triphenylphenol, 2-hydroxyfluorene, 9-anthracenemethanol, 2-methylphenanthrene, 2-naphthalene ethanol, 2-naphthyl-beta-d-galactopyranoside hydride, hydroxystyrene, styrene, acetoxystyrene, benzyl methacrylate, N-methyl maleimide, vinyl benzoate, vinyl 4-tert-butylbenzoate, ethylene glycol phenyl ether acrylate, phenoxypropyl acrylate, benzyl mevalonic lactone ester of maleic acid, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl) maleimide, 3-(4-acetoaminophenyl)azo-4-hydroxystyrene, 3-(4-ethoxycarbonyl phenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate. A skilled artisan will appreciate which chromophores are useful at the exposure wavelength of interest.

The polymer containing the acid labile unit may also contain other nonabsorbing monomeric units as described above. Examples of the polymer containing the acid labile group include copolymers of 2-methyl-2-adamantyl methacrylate, mevalonic lactone methacrylate, 3-hydroxy-1-adamantyl methacrylate, methacrylate ester of beta-hydroxy-gamma-butyrolactone, t-butyl norbornyl carboxylate, t-butyl methyl adamantyl methacrylate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris(trimethylsilyl)silyl ethyl ester of methyl methacrylate, with methyl methacrylate, butyl methacrylate, acrylic acid, methacrylic acid, vinyl alcohol, maleic anhydride, N-vinyl pyrrolidinone, maleimide, N-methyl maleimide, and the like.

Yet another polymer useful for the positive bottom photoimageable antireflective coating compositions is (iii) a polymer that comprises at least one unit with hydroxyl and/or carboxyl group and at least one unit with an absorbing chromophore. Examples of an absorbing chromophore are described hereinabove.

For the polymer comprising at least one unit with a hydroxyl and/or a carboxyl group to provide alkaline solubility, and a crosslinking site, one function of the polymer is to provide a good coating quality and another is to enable the antireflective coating to change solubility during the imaging process. The hydroxyl or carboxyl groups in the polymer provide one of the components necessary for the solubility change. Examples of monomers which provide such a unit upon polymerization are without limitations, substituted or unsubstituted vinyl monomers containing a hydroxyl and or carboxyl group, such as acrylic acid, methacrylic acid, vinyl alcohol, hydroxystyrenes, hydroxyethyl methacrylate, hydroxypropyl methacrylate, N-(hydroxymethyl)acrylamide, 4-hydroxyphenyloxy methacrylate, 4-hydroxyphenyloxy acrylate, 5-hydroxynaphthyloxy methacrylate, 5-hydroxynaphthyloxy acrylate, vinyl monomers containing 1,1', 2,2',3,3'-hexafluoro-2-propanol, although any monomer that makes the polymer alkali soluble and preferably water insoluble, may be used. The polymer may contain a mixture of monomer units containing hydroxyl and/or carboxyl groups. Vinyl monomers containing the 1,1,1,3,3,3-hexafluoro-2-propanol group are represented by structures (1) to (6) and their substituted equivalents.

(1)
(2)
(3)
(4)
(5)

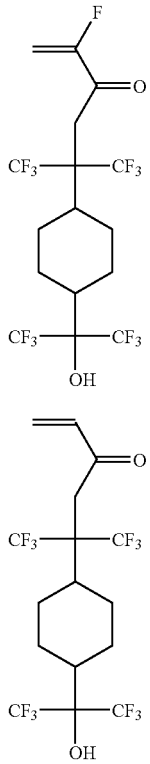
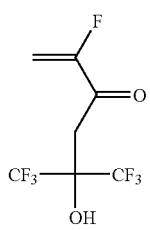
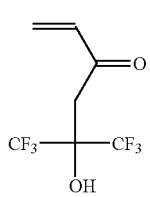
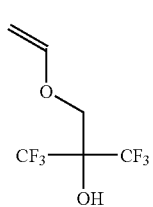

(6)

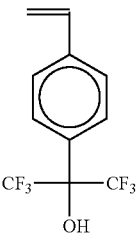

Thus a polymer may be synthesized by polymerizing monomers that contain a hydroxyl or carboxyl group with monomers that contain an absorbing chromophore. A skilled artisan will appreciate which chromophores are useful at the exposure wavelength of interest. Alternatively, the alkali soluble polymer may be reacted with compounds that provide the hydroxyl or carboxyl group and compounds that provide the absorbing chromophore. In the final polymer the mole % of the unit or units containing the hydroxyl or carboxyl group can range from 5 to 95, preferably 10 to 90, and more preferably 20 to 80 and the mole % of the absorbing chromophore unit in the final polymer can range from 5 to 95, preferably 10 to 90 more preferably 20 to 80. It is also within the scope of this invention that the hydroxyl or carboxyl group is attached to the absorbing chromophore or that the chromophore is attached to the hydroxyl or carboxyl group, that is, both groups are present in the same unit. As an example the chromophoric groups described previously may have pendant hydroxyl and/or carboxyl groups or that the chromophoric groups and the hydroxyl group and/or carbonyl group are attached to the same group.

In addition to the unit containing the hydroxyl and/or carboxyl group and the unit containing the absorbing chromophore, the polymer may contain other monomeric units, such units may provide other desirable properties, examples of which are described hererinabove.

Examples of the foregoing polymers include, for example,

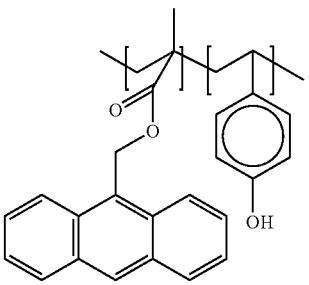

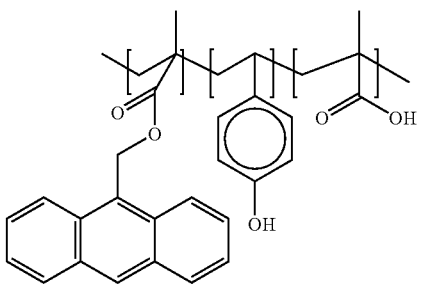

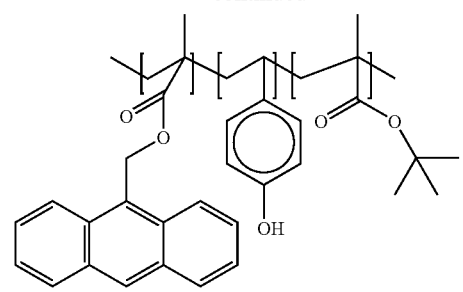
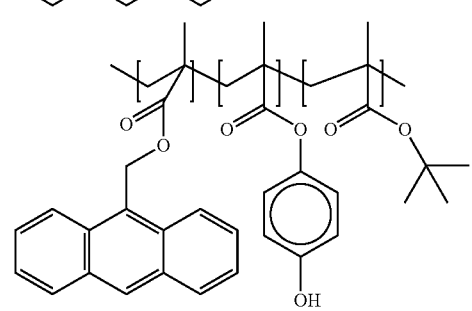
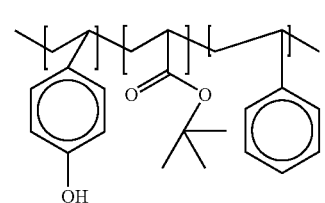
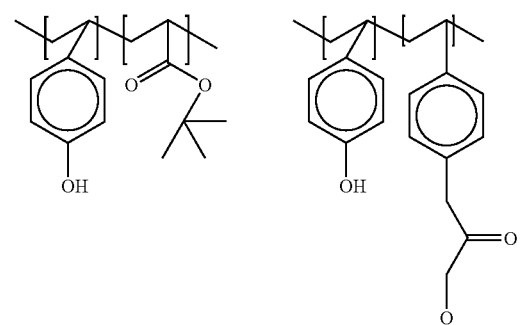
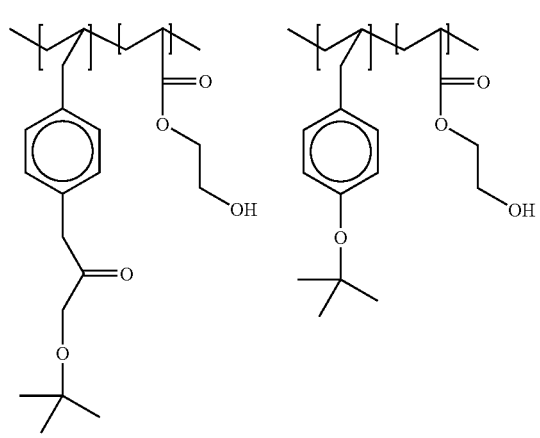
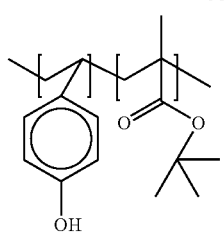
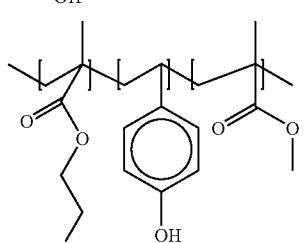
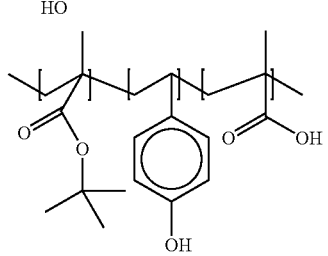
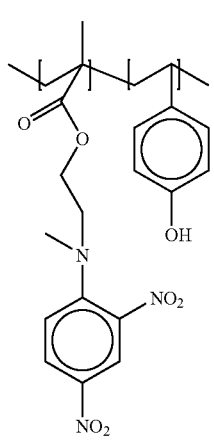
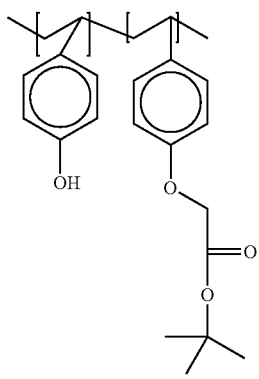
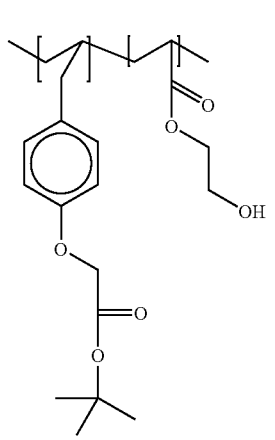

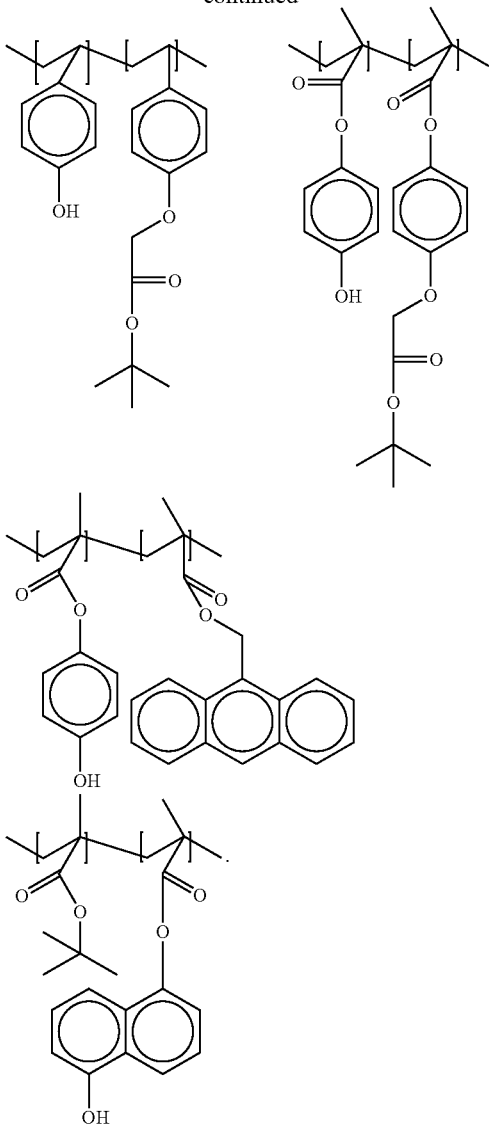

See also United States Published Patent Applications 20030129531 and 20050214674, the contents of which are hereby incorporated by reference herein.

When polymers having the hydroxyl and/or carboxyl group are used, a useful crosslinking agent to used therewith are vinyl ether terminated crosslinking agents that can be represented by the general structure (7):

wherein $R^1$ is selected from ($C_1$-$C_{30}$) linear, branched or cyclic alkyl, substituted or unsubstituted ($C_6$-$C_{40}$) aryl, or substituted or unsubstituted ($C_7$-$C_{40}$) alicyclic hydrocarbon; and $n \geq 2$. It is believed that the terminal vinyl ether group reacts with the hydroxyl or carboxyl group of the polymer to give an acid labile acetal linkage. Examples of such vinyl ether terminated crosslinking agents include bis(4-vinyloxy butyl) adipate; bis(4-vinyloxy butyl) succinate; bis(4-vinyloxy butyl) isophathalate; bis(4-vinyloxymethyl cyclohexylmethyl) glutarate; tris(4-vinyloxy butyl) trimellitate; bis(4-vinyloxy methyl cyclohexyl methyl) terephthalate; bis(4-vinyloxy methyl cyclohexyl methyl) isophthalate; bis(4-vinyloxy butyl) (4-methyl-1,3-phenylene) biscarbamate; bis (4-vinyloxy butyl)(methylene di-4,1-phenylene) biscarbamate; and triethyleneglycol divinylether, 1,4-cyclohexanedimentanol divinyl ether, various vinyl ether monomers available under the tradename Vectomer, such as, for example, 4-(vinyloxy)butyl benzoate, bis[4-(vinyloxy)butyl] adipate, bis[4-(vinyloxy)butyl]succinate, 4-(vinyloxymethyl)cyclohexylmethyl benzoate, bis[4-(vinyloxy)butyl] isophthalate, bis[4-(vinyloxymethyl)cyclohexylmethyl]glutarate, tris[4-(vinyloxy)butyl]trimellitate, 4-(vinyloxy)butyl stearate, bis[4-(vinyloxy)butyl]hexanediylbiscarbamate, bis [[4-[(vinyloxy)methyl]cyclohexyl]methyl]terephthalate, bis [[4-[(vi nyloxy)methyl]cyclohexyl]methyl] isophthalate, bis [4-(vinyloxy)butyl] (methylenedi-4,1-phenylene) biscarbamate, bis[4-(vinyloxy)butyl] (4-methyl-1,3-phenylene) biscarbamate, and polymers bearing pendant vinyloxy groups. Other vinyl ether terminated crosslinking agents are described in T. Yamaoka, et al., Trends in Photochem. Photobio., 7:45 (2001); S. Moon, et al., Chem. Mater., 6:1854 (1994); or H. Schacht, et al., ACS Symp. Ser. 706:78 (1998) which may also be used, and are incorporated herein by reference.

The vinyl ether terminated crosslinking agent is preferably added to the antireflective coating in a proportion which provides 0.20-2.00 mol equivalents of vinyl ether crosslinking function per reactive group on the polymer, especially preferred is 0.50-1.50 reactive equivalents per reactive group.

The foregoing polymers are typically used in positive bottom photoimageable antireflective coating compositions. For negative bottom photoimageable antireflective coating compositions, the following polymers are typically used.

For negative bottom photoimageable antireflective coating compositions, the polymer can comprise at least one unit which makes the polymer soluble in an aqueous alkaline developing solution. One function of the polymer is to provide a good coating quality and another is to enable the antireflective coating to change solubility from exposure to development. Examples of monomers that impart alkali solubility are acrylic acid, methacrylic acid, vinyl alcohol, maleimide, thiophene, N-hydroxymethyl acrylamide, N-vinyl pyrrolidinone. More examples are vinyl compounds of substituted and unsubstituted sulfophenyl and its tetraloweralkylammonium salts, substituted and unsubstituted hydroxycarbonylphenyl and its tetraloweralkylammonium salts such as 3-(4-sulfophenyl)azoacetoacetoxy ethyl methacrylate and its tetraloweralkylammonium salt, 3-(4-hydroxycarbonylphenyl)azoacetoacetoxy ethyl methacrylate and its tetraloweralkylammonium salt, N-(3-hydroxy-4-sulfophenylazo)phenyl methacrylamide and its tetraloweralkylammonium salt, N-(3-hydroxy-4-hydroxycarbonylphenylazo)phenyl methacrylamide and its tetraloweralkylammonium salt, where lower alkyl is H and $C_1$-$C_4$ groups.

Examples of monomers that can be cross linked are monomers with hydroxyl functionality such as hydroxyethyl methacrylate or those described in S. C. Fu et al. Proc. SPIE, Vol 4345, (2001) p. b751, monomers with acetal functionality, such as those described in UK Patent application 2,354,763 A and U.S. Pat. No. 6,322,948 B1, monomers with imide functionality, and monomers with carboxylic acid or anhydride functionality, such as are described in Naito et al. Proc. SPIE, vol. 3333 (1998), p. 503.

Examples of monomers include acrylic acid, methacrylic acid, vinyl alcohol, maleic anhydride, maleic acid, maleimide, N-methyl maleimide, N-hydroxymethyl acrylamide, N-vinyl pyrrolidinone. 3-(4-sulfophenyl)azoacetoacetoxy ethyl methacrylate and its tetrahydroammonium salt, 3-(4-hydroxycarbonylphenyl)azoacetoacetoxy ethyl methacrylate and its tetrahydroammonium salt, N-(3-hydroxy-4-hydroxycarbonylphenylazo)phenyl methacrylamide and its tetrahydroammonium salt. More preferred are groups acrylic acid, methacrylic acid, vinyl alcohol, maleic anhydride, maleic acid, maleimide, N-methyl maleimide, N-hydroxymethyl acrylamide, N-vinyl pyrrolidinone. tetrahydroammonium salt of 3-(4-sulfophenyl)azoacetoacetoxy ethyl methacrylate. The alkali soluble monomers may be polymerized to give homopolymers or with other monomers as required. The other monomers may be alkali insoluble, dyes, etc.

One polymer useful in the negative bottom photoimageable antireflective coating compositions contains at least one unit which is alkali soluble and at least one unit with an absorbing chromophore. Examples of an absorbing chromophore are hydrocarbon aromatic moieties and heterocyclic aromatic moieties with from one to four separate or fused rings, where there are 3 to 10 atoms in each ring. Examples of monomers with absorbing chromophores that can be polymerized with the monomers containing the acid labile groups are vinyl compounds containing substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Other chromophores are described in U.S. Pat. Nos. 6,114,085, 5,652,297, 5,981,145, 5,939,236, 5,935,760 and 6,187,506, which may also be used, and are incorporated herein by reference. Examples of such chromophores include vinyl compounds of substituted and unsubstituted phenyl, substituted and unsubstituted anthracyl, and substituted and unsubstituted naphthyl; and examples of such monomers include styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy)ethyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-nitrophenylazo)phenyl methacrylamide, N-(3-hydroxyl-4-ethoxycarbonylphenylazo)phenyl methacrylamide, N-(2,4-dinitrophenylaminophenyl)maleimide, 3-(4-acetoaminophenyl)azo-4-hydroxystyrene, 3-(4-ethoxycarbonyl phenyl)azo-acetoacetoxy ethyl methacrylate, 3-(4-hydroxyphenyl)azo-acetoacetoxy ethyl methacrylate, 3-(4-nitrophenyl)azoacetoacetoxy ethyl methacrylate, 3-(4-methoxycarbonyl phenyl)azoacetoacetoxy ethyl methacrylate.

Other than the unit containing the alkali soluble group and the absorbing chromophore, the polymer may contain other nonabsorbing, alkali insoluble monomeric units, such units may provide other desirable properties. Examples of the third monomer are —$CR_1R_2$—$CR_3R_4$—, where $R_1$ to $R_4$ are independently H, ($C_1$-$C_{10}$) alkyl, ($C_1$-$C_{10}$) alkoxy, nitro, halide, cyano, alkylaryl, alkenyl, dicyanovinyl, $SO_2CF_3$, COOZ, $SO_3Z$, COZ, OZ, $NZ_2$, SZ, $SO_2Z$, NHCOZ, $SO_2NZ_2$, where Z is ($C_1$-$C_{10}$) alkyl, hydroxy ($C_1$-$C_{10}$) alkyl, ($C_1$-$C_{10}$) alkyl$OCOCH_2COCH_3$, or $R_2$ and $R_4$ combine to form a cyclic group such as anhydride, pyridine, or pyrollidone.

Thus a polymer may be synthesized by polymerizing monomers that contain an alkali soluble group with monomers that contain an absorbing chromophore. Alternatively, the alkali soluble polymer may be reacted with compounds that provide the absorbing chromophore. The mole % of the alkali soluble unit in the final polymer can range from 5 to 95, preferably 30 to 70, more preferably 40 to 60, and the mole % of the absorbing chromophore unit in the final polymer can range from 5 to 95, preferably 30 to 70, more preferably 40 to 60. It is possible that the alkali soluble group is attached to the absorbing chromophore, or vice versa, for example, vinyl compounds of substituted and unsubstituted sulfophenyl and its tetraloweralkylammonium salts, substituted and unsubstituted hydroxycarbonylphenyl and its tetraloweralkylammonium salts such as 3-(4-sulfophenyl)azoacetoacetoxy ethyl methacrylate and its tetraloweralkylammonium salt, 3-(4-hydroxycarbonylphenyl)azoacetoacetoxy ethyl methacrylate and its tetraloweralkylammonium salt, N-(3-hydroxy-4-sulfophenylazo)phenyl methacrylamide and its tetraloweralkylammonium salt, N-(3-hydroxy-4-hydroxycarbonylphenylazo)phenyl methacrylamide and its tetraloweralkylammonium salt, where lower alkyl is H and $C_1$-$C_4$ groups.

Examples of polymers that contain both the alkali soluble group and the absorbing chromophore include copolymers of at least one of N methyl maleimide, N alkynol maleimide, acrylic acid, methacrylic acid, vinyl alcohol, maleic anhydride, maleic acid, maleimide, N-hydroxymethyl acrylamide, N-vinyl pyrrolidinone. 3-(4-sulfophenyl)azoacetoacetoxy ethyl methacrylate and its tetrahydroammonium salt, 3-(4-hydroxycarbonylphenyl)azoacetoacetoxy ethyl methacrylate and its tetrahydroammonium salt, N-(3-hydroxy-4-hydroxycarbonylphenylazo)phenyl methacrylamide and its tetrahydroammonium salt, with at least one of styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy) ethyl acrylate, 2-hydroxy-3-phenoxypropyl acrylate, phenyl methacrylate, benzyl methacrylate, 9-anthcenylmethyl methacrylate, 9-vinylanthracene, 2-vinylnaphthalene, N-vinylphthalimide, N-(3-hydroxy)phenyl methacrylamide, N-(3-hydroxy-4-nitrophenylazo)phenyl methacrylamide, N-(3-hydroxyl-4-ethoxycarbonylphenylazo)phenyl methacrylamide, N-(2,4-dinitrophenylaminophenyl)maleimide, 3-(4-acetoaminophenyl)azo-4-hydroxystyrene, 3-(4-ethoxycarbonyl phenyl)azo-acetoacetoxy ethyl methacrylate, 3-(4-hydroxyphenyl)azo-acetoacetoxy ethyl methacrylate, 3-(4-nitrophenyl)azoacetoacetoxy ethyl methacrylate, 3-(4-methoxycarbonyl phenyl)azoacetoacetoxy ethyl methacrylate.

Another polymer useful in the negative bottom photoimageable antireflective coating compositions is a polymer with at least one unit which makes the polymer soluble in an aqueous alkaline developing solution, a dye, a crosslinking agent and a photoacid generator. The absorption necessary for the antireflective coating is provided not by the unit in the polymer, but by the incorporation of an additive that absorbs at the exposure wavelength. The dye may be incorporated into the polymer or as an additive in the composition. This dye may be monomeric, polymeric or mixtures of both. Examples of such dyes are substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Absorbing polymeric dyes that may be used are polymers of the absorbing moieties listed above, where the polymer backbone may be polyesters, polyimides, polysulfones and polycarbonates. Some of the dyes are copolymers of hydroxystyrene and methyl methacrylate, such as disclosed in U.S. Pat. No. 6,114,085, and azo polymeric dyes, such as disclosed in U.S. Pat. Nos. 5,652,297, 5,763,135, 5,981,145, 5,939,236 , 5,935,760, and 6,187,506, all of which are incorporated herein by reference. Examples of monomers or homo- or co-polymers of as triphenylphenol, 2-hydroxyfluorene, 9-anthracenemethanol, 2-methylphenanthrene, 2-naphthaleneethanol, 2-naphthyl-beta-d-galactopyranoside hydride, benzyl mevalonic lactone ester of maleic acid, 3-(4-sulfophenyl)azoacetoacetoxy ethyl methacrylate and its tetrahydroammonium salt, 3-(4-hydroxycarbonylphenyl)azoacetoacetoxy ethyl methacrylate and its tetrahydroammonium salt, N-(3-hydroxy-4-hydroxycarbonylphenylazo)phenyl methacrylamide and its tetrahydroammonium salt, styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy)ethyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-nitrophenylazo)phenyl methacrylamide, N-(3-hydroxyl-4-ethoxycarbonylphenylazo) phenyl methacrylamide, N-(2,4-dinitrophenylaminophenyl)maleimide, 3-(4-acetoaminophenyl)azo-4-hydroxystyrene, 3-(4-ethoxycarbonyl phenyl)azo-acetoacetoxy ethyl methacrylate, 3-(4-hydroxyphenyl)azo-acetoacetoxy ethyl methacrylate, 3-(4-nitrophenyl)azoacetoacetoxy ethyl methacrylate, 3-(4-methoxycarbonyl phenyl)azoacetoacetoxy ethyl methacrylate.

Examples of such polymers include copolymers of acrylic acid, methacrylic acid, vinyl alcohol, maleic anhydride, thiophenes maleic acid, maleimide, N-methyl maleimide, N-vinyl pyrrolidinone or mixtures thereof, with methyl methacrylate, butyl methacrylate, hydroxyethyl methacrylate, hydroxypropyl methacrylate, styrene, hydroxystyrene or mixtures thereof.

Another polymer useful in the negative bottom photoimageable antireflective coating compositions is a polymer that changes polarity or functionality in the presence of the photolyzed photoactive compound such that its solubility in aqueous base is changed from soluble to insoluble after exposure. The absorbance can be intrinsic to the polymer or due to an added dye. The polymer is synthesized from, for example, monomers that change functionality or polarity in the presence of acid, such as monomers containing gamma hydroxy carboxylic acids which lactonize in the presence of acid, such as is described in Yokoyama et al. Proc. SPIE, Vol. 4345, (2001), p. 58-66 and Yokoyama et al. J. of Photopolymer Sci. and Techn. Volume 14, No. 3, p. 393. Another example of such a monomer is a monomer containing a pinacol functionality, such as that described in S. Cho et al., Proc SPIE, Vol. 3999, (2000) pps. 62-73. The change in solubility is not due to a crosslinking mechanism.

Examples of the foregoing polymers useful with negative bottom photoimageable antireflective coating compositions include:

a copolymer of at least one of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl)azoacetoacetoxy ethyl methacrylate, 3-(4-hydroxycarbonylphenyl)azoacetoacetoxy ethyl methacrylate or mixtures thereof, with at least one of maleimide, N-methyl maleimide, N-methylol maleimide, vinyl alcohol, allyl alcohol, acrylic acid, methacrylic acid, maleic anhydride, thiophene, methacrylate ester of beta-hydroxy-gamma-butyrolactone, 2-methyl-2-adamantyl methacrylate, 3-hydroxy-1-adamantyl methacrylate, methacrylate ester of mevalonic lactone, or mixtures thereof; further exemplified by a polymer of hydroxystyrene, styrene and N-methyl maleimide, where preferably the maleimide ranges from 30 to 70 mole %, styrene ranges from 5 to 50 mole % and hydroxystyrene ranges from 5 to 50 mole %, more preferably maleimide ranges from 40 to 60 mole %, styrene ranges from 10 to 40 mole % and hydroxystyrene ranges from 10 to 40 mole %, and even more preferably styrene and hydroxystyrene each range from 20 to 30 mole %;

a copolymer of at least one of maleimide, N-methylmaleimide, vinyl alcohol, allyl alcohol, acrylic acid, methacrylic acid, maleic anhydride, thiophene, methacrylate ester of beta-hydroxy-gamma-butyrolactone, 2-methyl-2-adamantyl methacrylate, with at least one of methyl methacrylate, hydroxyethyl methacrylate, 3-hydroxy-1-adamantyl methacrylate, styrene, hydroxystyrene and methacrylate eater of mevalonic lactone;

a copolymer of at least one monomer of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl)azoacetoacetoxy ethyl methacrylate, and 3-(4-hydroxycarbonylphenyl)azoacetoacetoxy ethyl methacrylate, with at least one monomer of maleic anhydride or maleimide and 5(2,3-dihydroxy-2,3-dimethyl)butylbicyclo[2.2.1]hept-2-ene;

a copolymer of at least one monomer of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl)azoacetoacetoxy ethyl methacrylate, and 3-(4-hydroxycarbonylphenyl)azoacetoacetoxy ethyl methacrylate, with at least one monomer of maleic anhydride that has been treated with sodium borohydride to reduce the polymer bound anhydride to a gamma hydroxy acid;

a copolymer of at least one monomer of maleic anhydride norbornene that has been treated with sodium borohydride to reduce the polymer bound anhydride to a gamma hydroxy lactone;

a copolymer of at least one monomer of maleimide or maleic anhydride and 5(2,3-dihydroxy-2,3-dimethyl)butylbicyclo[2.2.1]hept-2-ene.

The polymers may be synthesized using any known method of polymerization, such as ring-opening metathesis, free-radical polymerization, condensation polymerization, using metal organic catalysts, or anionic or cationic copolymerization techniques. The polymer may be synthesized using solution, emulsion, bulk, suspension polymerization, or the like. The polymers of this invention are polymerized to give a polymer with a weight average molecular weight from about 1,000 to about 1,000,000, preferably from about 2,000 to about 80,000, more preferably from about 4,000 to about 50,000. When the weight average molecular weight is below 1,000, then good film forming properties are not obtained for the antireflective coating and when the weight average molecular weight is too high, then properties such as solubility, storage stability and the like may be compromised. The polydispersity (Mw/Mn) of the free-radical polymers, where Mw is the weight average molecular weight and Mn is the number average molecular weight, can range from 1.5 to 10.0, where the molecular weights of the polymer may be determined by gel permeation chromatography.

The negative photoimageable antireflective coating composition can also contain a crosslinking agent. A variety of crosslinking agents can be used in the composition of the present invention. Any suitable crosslinking agent that can crosslink the polymer in the presence of an acid may be used. Any of the crosslinking agents known in the art may be used, such as those disclosed in U.S. Pat. Nos. 5,886,102 and 5,919, 599, and which are incorporated herein by reference. Examples of such crosslinking agents are melamines, methylols, glycolurils, hydroxy alkyl amides, epoxy and epoxy amine resins, blocked isocyanates, and divinyl monomers. Melamines like hexamethoxymethyl melamine and hexabutoxymethylmelamine; glycolurils like tetrakis(methoxymethyl)glycoluril and tetrabutoxyglycoluril; and aromatic methylols, like 2,6 bishydroxymethyl p-cresol are preferred. Other crosslinkers are tertiary diols such as 2,5-dimethyl-2, 5-hexanediol, 2,4-dimethyl-2,4-pentanediol, pinacol, 1-methylcyclohexanol, tetramethyl-1,3-benzenedimethanol, and tetramethyl-1,4-benzenedimethanol, and polyphenols, such as tetramethyl-1,3-benzenedimethanol.

Examples of negative bottom photoimageable antireflective coating compositions include

[A] 1) a copolymer of at least one of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl)azoacetoacetoxy ethyl methacrylate, 3-(4-hydroxycarbonylphenyl) azoacetoacetoxy ethyl methacrylate or mixtures thereof, with at least one of maleimide, N-methyl maleimide, N-methylol maleimide, vinyl alcohol, allyl alcohol, acrylic acid, methacrylic acid, maleic anhydride, thiophene, methacrylate ester of beta-hydroxy-gamma-butyrolactone, 2-methyl-2-adamantyl methacrylate, 3-hydroxy-1-adamantyl methacrylate, methacrylate ester of mevalonic lactone, or mixtures thereof 2) a crosslinker such as tetrakis(methoxymethyl)glycoluril and hexaalkoxymethylmelamine, 3) a photoacid generator as disclosed herein, 4) optionally, some additives such as amine and surfactant, and 5) solvent or mixtures of solvents such as propylene glycol monomethyl ether acetate, propylene glycol monomethyl ether, and ethyl lactate;

[B] 1) a copolymer of at least one of maleimide, N-methylmaleimide, vinyl alcohol, allyl alcohol, acrylic acid, methacrylic acid, maleic anhydride, thiophene, methacrylate ester of beta-hydroxy-gamma-butyrolactone, 2-methyl-2-adamantyl methacrylate, with at least one of methyl methacrylate, hydroxyethyl methacrylate, 3-hydroxy-1-adamantyl methacrylate, styrene, hydroxystyrene and methacrylate eater of mevalonic lactone, 2) a dye such as triphenylphenol, 9-anthracenemethanol, benzyl mevalonic lactone ester of maleic acid, polymer of benzyl methacrylate, hydroxystyrene, 9-anthracenylmethyl methacrylate, and 3-acetoaminophenylazo-4-hydroxystyrene with methyl methacrylate and hydroxyethyl methacrylate, 3) a crosslinker such as tetrakis(methoxymethyl)glycoluril and hexaalkoxymethylmelamine, 4) a photoacid generator as disclosed herein, optionally, 4) some additives such as amine and surfactant, and 5) solvent or mixtures of solvents such as propylene glycol monomethyl ether acetate, propylene glycol monomethyl ether, and ethyl lactate;

[C] 1) a copolymer of at least one monomer of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl)azoacetoacetoxy ethyl methacrylate, and 3-(4-hydroxycarbonylphenyl)azoacetoacetoxy ethyl methacrylate, with at least one monomer of maleic anhydride or maleimide and 5(2,3-dihydroxy-2,3-dimethyl)butylbicyclo[2.2.1]hept-2-ene, 2) a photoacid generator as disclosed herein, optionally, 4) some additives such as amine and surfactant, and 5) solvent or mixtures of solvents such as propylene glycol monomethyl ether acetate, propylene glycol monomethyl ether, and ethyl lactate;

[D] 1) a copolymer of at least one monomer of acetoxystyrene, hydroxystyrene, styrene, benzyl methacrylate, phenyl methacrylate, 9-anthracenylmethyl methacrylate, 9-vinylanthracene, 3-(4-methoxycarbonylphenyl) azoacetoacetoxy ethyl methacrylate, and 3-(4-hydroxycarbonylphenyl)azoacetoacetoxy ethyl methacrylate, with at least one monomer of maleic anhydride that has been treated with sodium borohydride to reduce the polymer bound anhydride to a gamma hydroxy acid, 2) a photoacid generator as disclosed herein, and optionally, 3) some additives such as amine and surfactant, and 4) solvent or mixtures of solvents such as propylene glycol monomethyl ether acetate, propylene glycol monomethyl ether, and ethyl lactate;

[E] 1) a copolymer of at least one monomer of maleic anhydride norbornene that has been treated with sodium borohydride to reduce the polymer bound anhydride to a gamma hydroxy lactone, 2) a dye such as triphenylphenol, 9-anthracenemethanol, benzyl mevalonic lactone ester of maleic acid, polymer of benzyl methacrylate, hydroxystyrene, 9-anthracenylmethyl methacrylate, and 3-acetoaminophenylazo-4-hydroxystyrene with methyl methacrylate and hydroxyethyl methacrylate, 3) a photoacid generator as disclosed herein, optionally, 4) some additives such as amine, and 5) solvent or mixtures of solvents such as propylene glycol monomethyl ether acetate, propylene glycol monomethyl ether, and ethyl lactate;

[F] 1) a copolymer of at least one monomer of maleimide or maleic anhydride and 5(2,3-dihydroxy-2,3-dimethyl)butylbicyclo[2.2.1]hept-2-ene, 2) a dye such as triphenylphenol, 9-anthracenemethanol, benzyl mevalonic lactone ester of maleic acid, polymer of benzyl methacrylate, hydroxystyrene, 9-anthracenylmethyl methacrylate, and 3-acetoaminophenylazo-4-hydroxystyrene with methyl methacrylate and hydroxyethyl methacrylate, 3) a photoacid generator as disclosed herein, and 2,1,4-diazonaphthoquinones, optionally, 4) some additives such as amine, and 5) solvent or mixtures of solvents such as propylene glycol monomethyl ether acetate, propylene glycol monomethyl ether, and ethyl lactate.

The compositions of the present invention may further comprise an acid or a thermal acid generator. Crosslinking can take place between a polymer containing a hydroxyl and/or carboxyl group and a crosslinking agent in the presence of heat, however, typically reaction times may be long. Thermal acid generators or acids are used to accelerate the crosslinking reaction and are desirable for instances where short curing times are preferred. Thermal acid generators liberate the acid upon heating. Any known acids or thermal acid generators may be used, exemplified without limitations, by 2,4,4,6-tetrabromocyclohexadienone, benzoin tosylate, squaric acid, 2-nitrobenzyl tosylate, chloroacetic acid, toluenesulfonic acid, methanesulfonic acid, nonaflate acid, triflic acid, other alkyl esters of organic sulfonic acids, salts of these mentioned acids. However, it has been found that for certain components some acids and acids produced by thermal acid generators, which have high acidity, can lead to undercutting and can prevent the desired photoimaging process from taking place.

Thus, it has been unexpectedly found that acids with moderate acidity, i.e. with a pKa ($-\log_{10}$ of the acid dissociation constant) greater than 1.0 are preferred, especially in combination with a vinyl terminated crosslinking agent. Acids with a pKa of less than 5.0 and greater than 1.0 are also preferred. The resulting acetal linkages are easily cleavable in the presence of photogenerated acids. Examples, without limitations, of acids or acids derived from thermal acid generators with moderate acidity are maleic acid (pKa of 1.83), chloroacetic acid (pKa of 1.4), dichloroacetic acid (pKa of 1.48), oxalic acid (pKa of 1.3), cinnamic acid (pKa of 4.45), tartaric acid (pKa of 4.3), gylcolic acid (pKa of 3.8), fumaric acid (pKa of 4.45), malonic acid (pKa of 2.8), cyanoacetic acid (pKa of 2.7), etc.

Acids which are blocked by bases to form a thermal acid generator are preferred. Acids, such as those described above, may be blocked with bases such as amines. Typical bases are triethyl amine, tripropyl amine, trimethyl amine, tributyl amine, tripentyl amine, tridodecyl amine etc. Additionally, diaryl or trialkyl sulfonium salts with anions of weak acids, such as carboxylic acid or aryl carboxylic acid may be used. Acids which are blocked by bases may be formed by combining the acid with a base, where the acid:base ratio ranges from about 1:1 to about 1:3. Further examples of acids with the desired pKa and their salts can be found by one of ordinary skill in the art by reviewing the available literature, such as in CRC Handbook of Chemistry and Physics, published by CRC Press Inc. and incorporated herein by reference. In some embodiments it may also be desirable that the thermal acid be such that once the acid is generated it does not remain permanently in the coating and therefore does not facilitate the reverse reaction, but is removed from the film. It is believed that, once crosslinking takes place the acid is decomposed or volatilized by heat and the decomposition products are baked out of the film, or the acid may sublime from the coating. Thus none or very little of the free acid remains in the film after curing, and the reverse reaction causing the decomposition of the acetal linkage does not take place. Thermal acid generators which can generate an acid and then be removed prior to coating of the photoresist are preferred in some cases. Weak acids that remain in the film may also be functional, as they may not greatly hinder the decomposition of the acetal linkage. The amines used are typically volatile ones, the use of which providing significant benefits in that the amine can be removed (volatized) from the antireflective composition coating layer during thermal curing of that layer.

One interesting class of thermal acid generators is based on mono functionalized ammonium salts of dicarboxylic acids. These mono functional ammonium salts of dicarboxylic acid have been found to decompose at lower temperatures. Because of their low decomposition temperature, some of which are as low as about 115° C. (based on TGA onset temperature), these acids are useful, for example, in forming reversible cross-linked networks in developable bottom antireflective coatings which contain, for example, hydroxyl moieties and vinlyoxy compounds. These acids are beneficial in providing that less reversal of the cross-linking reaction occurs upon cooling, giving rise to a more cross-linked developable bottom antireflective coating film which is less susceptible to erosion. Also, with low decomposition temperatures, this allows any residual thermal acid generators to be eliminated from the antireflective coating at lower temperatures, which in turn could reduce the baking temperature of the antireflective coating composition.

The acid or acid derived from the thermal acid generator is preferably removed from the antireflective coating (decomposes) at a temperature ranging from about 115° C. to about 220° C., further from 120° C. to about 200° C.

The mono functionalized ammonium salts of dicarboxylic acid has the general formula

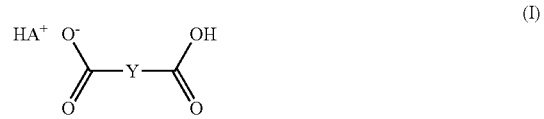

(I)

where Y is selected from a direct bond and a connecting group; and A is an unsubstituted or substituted amine compound.

The connecting group Y can be selected from $C_1$-$C_8$ unsubstituted or substituted alkylene chain optionally containing one or more hetero atoms (for example, O, S, SO, $SO_2$, —C(=O)—, —C(=O)O—, —O—C(=O)—O—, —OC(=O)—), $C_3$-$C_8$ unsubstituted or substituted cycloalkylene, $C_2$-$C_8$ unsubstituted or substituted alkenylene, and $C_6$-$C_{12}$ unsubstituted or substituted arylene. Furthermore, it can be $C_1$-$C_8$ unsubstituted or substituted alkylene chain optionally containing one or more hetero atoms, even still, $C_1$-$C_8$ unsubstituted or substituted alkylene chain optionally containing one or more O atoms, and yet even still $C_1$-$C_8$ unsubstituted or substituted alkylene chain (for example, unsubstituted or substituted methylene; unsubstituted or substituted ethylene; or unsubstituted or substituted propylene), $C_1$-$C_3$ unsubstituted or substituted alkylene chain, or even $C_1$-$C_3$ alkylene chain substituted with hydroxyl and/or alkyl.

The amine compound can be selected such that it volatizes at a temperature at which compositions which contain the compound of formula (I) are baked. Examples of the amine compound include a compound selected from the group consisting of

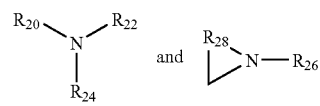

where each of $R_{20}$, $R_{22}$, $R_{24}$, and $R_{26}$ are individually selected from hydrogen, unsubstituted or substituted alkyl, unsubstituted or substituted cycloalkyl, unsubstituted or substituted monocyclic or polycyclic aryl, and unsubstituted or substituted aralkyl; and $R_{28}$ is selected from $C_3$-$C_7$ unsubstituted or substituted alkylene or $R_{28}$ together with the atoms to which it is bound forms a $C_6$-$C_{12}$ unsubstituted or substituted monocyclic or polycyclic aryl. Further examples include ammonia, unsubstituted and substituted trialkylamines, unsubstituted and substituted dialkylamines, and unsubstituted and substituted monoalkylamines, unsubstituted and substituted tricycloalkylamines, unsubstituted and substituted dicycloalkylamines, and unsubstituted and substituted monocycloalkylamines, unsubstituted and substituted monocylcoalkyldialkylamines, unsubstituted and substituted dicycloalkylmonoalkylamines, unsubstituted and substituted monoaryldialkylamines, unsubstituted and substituted diarylmonoalkylamines, unsubstituted and substituted triarylamines, unsubstituted and substituted diarylamines, and unsubstituted and substituted monoarylamines, unsubstituted and substituted triaralkylamines, unsubstituted and substituted diaralkylamines, and unsubstituted and substituted monoaralkylamines, unsubstituted and substituted monoaralkyldialkylamines, unsubstituted and substituted diaralkylmonoalkylamines, unsubstituted and substituted monoarylmonoalkylamines, unsubstituted and substituted monoarallylmonoalkylamines, unsubstituted and substituted monocycloalkylmonoalkylamines, and unsubstituted and substituted monoarylmonocycloalkylamines and the like, etc. Further examples include trimethylamine, dimethylethylamine, dimethylpropylamine, dimethylbutylamine, methyldiethylamine, methyldipropylamine, methyldibutylamine, methylethylpropylamine, methylethylbutylamine, methylpropylbutylamine, triethylamine, ethyldipropylamine, ethyldibutylamine, diethylpropylamine, diethylbutylamine, ethylpropylbutylamine, tripropylamine, dipropylbutylamine, propyldibutylamine, tributylamine, pyrrolidine, piperidine, piperazine, cyclohexyl amine, and the like, etc.

As used herein, alkyl means methyl, ethyl, propyl (n-propyl, i-propyl), butyl (n-butyl, i-butyl, sec-butyl, t-butyl), pentyl (and its isomers), hexyl (and its isomers), heptyl (and its isomers), octyl (and its isomers), and the like. The cycloalkyls include cyclohexyl, menthyl and the like. The alkenyls include allyl, vinyl and the like. The aryl groups include monocyclic or polycyclic rings such as, for example, phenyl, naphthyl and the like. The aralkyl groups include phenylmethyl (i.e., benzyl), phenylethyl (i.e., phenethyl) and the like. Alkylene, cycloalkylene, and arylene mean the same as above for alkyl, cycloalkyl, and aryl except that an additional hydrogen atom has been removed from the alkyl, cycloalkyl or aryl (for example, ethylene, propylene, cyclohexylene, phenylene, etc).

We have found that when dicarboxylic acids are reacted with an excess of an amine, such as, for example, triethylamine only the monofunctional salt can be isolated. This was confirmed by infrared spectroscopic analysis, proton NMR and elemental analysis. IR analysis shows that all the difunctional acid had two carbonyl peaks corresponding to carboxylic moieties in both the acid form (—$CO_2H$) and carboxylate form (—$CO_2^-$). This is in contrast to what is found in the spectra of ammonium salts of monofunctional carboxylic acid which only give one peak at ~1600-1620 $cm^{-1}$. Similarly, the elemental analysis gave results which are consistent with only one ammonium moiety per acid despite the use of two moles of triethylamine per mole of difunctional acid.

In terms of thermal decomposition, these compounds start to decompose as judged by either TGA onset temperature or by irreversible transitions seen in DSC at a temperature between about 115 and about 140° C. (Table 1). The glutarate and succinate salts give higher onset temperatures but lose comparable amounts of wt the lower temperatures compared to the other salts. It is believed that these materials undergo similar decomposition temperatures to yield the free acid, but once this happens, the acids generated decompose at different temperatures. For example, the malonic acid derivatives (~135° C. decomp) and malic acid (~140° C. decomp) are know to have low decomposition temperatures while oxalic (~190° C. mp/decomp), glutaric (304° C. bp/decomp), succinic (235° C. bp/decomp) have much higher decomposition temperatures (acid decomposition temperature from Merck Index Tenth Edition, Martha Windholz Editor 1983).

TABLE 1

|  | TGA Onset (° C.) | DSC irreversible transitions (° C.) |
| --- | --- | --- |
| Monotriethylammonium oxalate | 129, 188 | 141, 159, 178 |
| Monotriethylammonium malonate | 125 | 135 |
| Monotriethylammonium 1-butylmalonate | 115 | 137 |
| Monotriethylammonium malate | 179 | 130, 180 |

TABLE 1-continued

|  | TGA Onset (° C.) | DSC irreversible transitions (° C.) |
| --- | --- | --- |
| Monotriethylammonium succinate | 197 | 128, 166 |
| Monotriethylammonium glutarate | 196 | 137, 152, 206 |

* Thermal analysis done at a heating rate of 10° C. per min

The acid or acid derived from the thermal acid generator preferably is removed (decomposes) from the coating at a temperature ranging from about 115° C. to about 220° C., further from 120° C. to about 200° C.

Examples of the compounds of formula (I) include

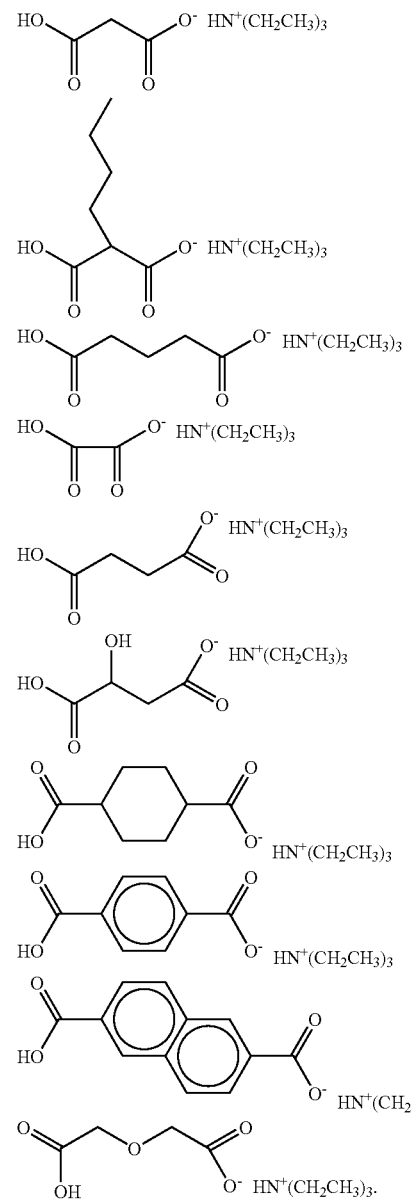

The photoacid generator used in the positive or negative bottom photoimageable antireflective coating compositions should be substantially insoluble in the solvent used in the photoresist (for example, equal to or less than 3 wt % solubility in PGMEA). It has been found that the insolubility of the photoacid generator in the solvent of the photoresist is related to the volume of the cation and anion portions of the photoacid generator and can be further viewed in conjunction with the melting point of the photoacid generator.

For example, if a monovalent cation has a volume less than or equal to about 243 Å$^3$, the maximum volume of a corresponding monovalent anion is less than or equal to about 196 Å$^3$. In certain instances, the melting point of a photoacid generator where the monovalent cation has a volume less than or equal to about 243 Å$^3$ and the maximum volume of the corresponding monovalent anion is less than or equal to about 196 Å$^3$, the melting point is greater than about 130° C.

Additionally, if a monovalent cation has a volume less than or equal to about 440 Å$^3$, the maximum volume of a corresponding monovalent anion less than or equal to about 83 Å$^3$. In certain instances, where the monovalent cation has a volume less than or equal to about 440 Å$^3$ and the maximum volume of a corresponding monovalent anion less than or equal to about 83 Å$^3$, the melting point of the photoacid generator is greater than about 200° C.

In other instances, a monovalent cation can be paired with a divalent anion. In this instance, it has been found that when the divalent anion size is less than or equal to about 196 Å$^3$, the monovalent cation has a volume less than or equal to about 440 Å$^3$. In this instance, the melting point of the photoacid generator is greater than about 80° C.

In yet further instances, a monovalent cation can be paired with a trivalent anion. In this instance, it has been found that when the trivalent anion size is less than or equal to about 220 Å$^3$, the monovalent cation has a volume less than or equal to about 440 Å$^3$. In this instance, the melting point of the photoacid generator is greater than about 80° C.

In another instance, a divalent cation can be paired with a monovalent anion. In this instance, it has been found that when the divalent cation size is less than or equal to about 450 Å$^3$, the monovalent anion has a volume less than or equal to about 161 Å$^3$. In this instance, the melting point of the photoacid generator is greater than about 130° C.

Thus, the photoacid generator having a cation and an anion can be selected from the following:

An example where the cation is a monovalent cation with a volume of less than or equal to about 450 cubic angstroms, the anion is a monovalent anion with a volume of less than or equal to about 84 cubic angstroms, and the photoacid generator has a melting point of at least 200° C. is tris(4-tert-butylphenyl)sulfonium triflate.

Examples where the cation is a monovalent cation with a volume of less than or equal to about 245 cubic angstroms, the anion is a monovalent anion with a volume of less than or equal to about 200 cubic angstroms, and the photoacid generator has a melting point of at least 130° C. include triphenylsulfonium triflate, triphenylsulfonium cyclamate, and triphenylsulfonium camphorsulfonate Examples where the cation is a monovalent cation with a volume of less than or equal to about 450 cubic angstroms, the anion is a divalent anion with a volume of less than or equal to about 205 cubic angstroms, and the photoacid generator has a melting point of at least 80° C. include bis(triphenylsulfonium) methanedisulfonate, bis-(triphenyl)sulfonium-1,3-propanedisulfonate, bis(triphenylsulfonium)perfluorobutanedisulfonate, bis-tris(4-tertbutylphenyl) sulfonium methanedisulfonate, bis-tris(4-tertbutylphenyl)sulfonium-1,2-ethanedisulfonate, and bis-tris(4-tertbutylphenyl)sulfonium 1,3-propanedisulfonate.

Examples where the cation is a monovalent cation with a volume of less than or equal to about 450 cubic angstroms, the anion is a trivalent anion with a volume of less than or equal to about 220 cubic angstroms, and the photoacid generator has a melting point of at least 80° C. include tris bis(4-tert-butylphenyl)iodonium-1,3,5-benzenetrisulfonate, and tris tris(4-tertbutylphenyl)sulfonium-1,3,5-benzenetrisulfonate An example where the cation is a divalent cation with a volume of less than or equal to about 450 cubic angstroms, the anion is a monovalent anion with a volume of less than or equal to about 165 cubic angstroms, and the photoacid generator has a melting point of at least 130° C. is (thiodi-4,1-phenylene)bisdiphenylsulfonium nonaflate.

Mixtures of the foregoing photoacid generators are also envisioned.

The volumes of anion and cation were done using Molecular Modeling Pro plus version 6.1.6 by Norgwyn Montgomery Software.

As mentioned above, in some instances, the anion can be multifunctional. Thus, the photoacid generator can have the general formula

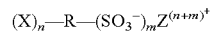

where X is anionic group selected from SO$_3^-$, SO$_2^-$, CO$_2^-$, and PO$_3^{-2}$; m and n are each integers from 1 to 3; R is a spacer group selected from linear or branched alkyl, cycloalkyl, aryl, or combinations thereof, optionally containing a catenary O, S or N, where the alkyl, cycloalkyl, and aryl groups are unsubstituted or substituted by one or more groups selected from the group consisting of halogen, unsubstituted or substituted alkyl, unsubstituted or substituted C$_{1-8}$ perfluoroalkyl, hydroxyl, cyano, sulfate, and nitro; and Z is a cation. Further examples of these types of photoacid generators can be found in United States Published Patent Application No. 20070015084, the contents of which are hereby incorporated herein by reference. Other examples are found in U.S. patent application Ser. No. 11/355,400, filed Feb. 16, 2006, United States Published Patent Application 2004-0229155, and United States Published Patent Application 2005-0271974, U.S. Pat. Nos. 5,837,420, 6,111,143, and 6,358,665, the contents of which are hereby incorporated herein by reference.

Examples of such anions include $^-$O$_3$S—CH$_2$—SO$_3^-$, $^-$O$_3$S—CH$_2$CH$_2$—CO$_2^-$, $^-$O$_3$S—(CF$_2$)$_4$—SO$_3^-$, $^-$O$_3$S—CH$_2$CH$_2$—SO$_3^-$, $^-$O$_3$S—CH$_2$CH$_2$CH$_2$—SO$_3^-$, CH(SO$_3^-$)$_3$,

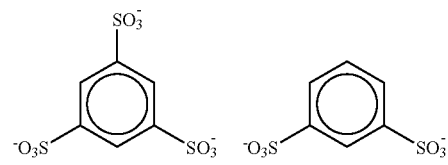

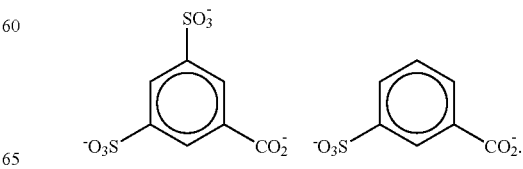

Examples of cation Z include

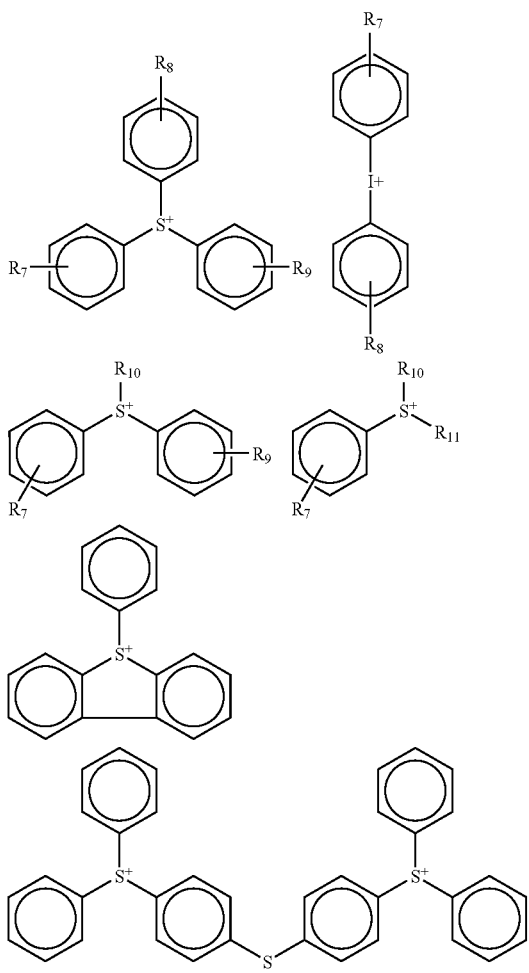

where $R_7$, $R_8$, and $R_9$, are each individually selected from hydrogen, alkyl, aryl, alkoxy, alkoxycarbonyl, and halogen, where the alkyl, aryl, alkoxy, and alkoxycarbonyl are unsubstituted or substituted; and $R_{10}$ and $R_{11}$ are each individually selected from hydrogen, alkyl, and cycloalkyl where the alkyl and cycloalkyl are unsubstituted or substituted.

In another instance, the anion can have a small size and the cation is also small in size and/or symmetric in shape. A general formula for such a photoacid generator is

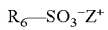

where $R_6$ is, for example, unsubstituted or substituted alkyl, unsubstituted or substituted monocyclo- or polycycloalkyl partially fluorinated alkyl, or perfluoroalkyl. Examples of anion include $CH_3-SO_3^-$, $CH_3CH_2-SO_3^-$, $CF_3-SO_3^-$, $CF_3CH_2-SO_3^-$,

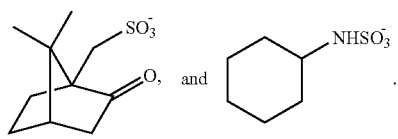

The general formula of cation Z is shown above. Examples of cation Z include

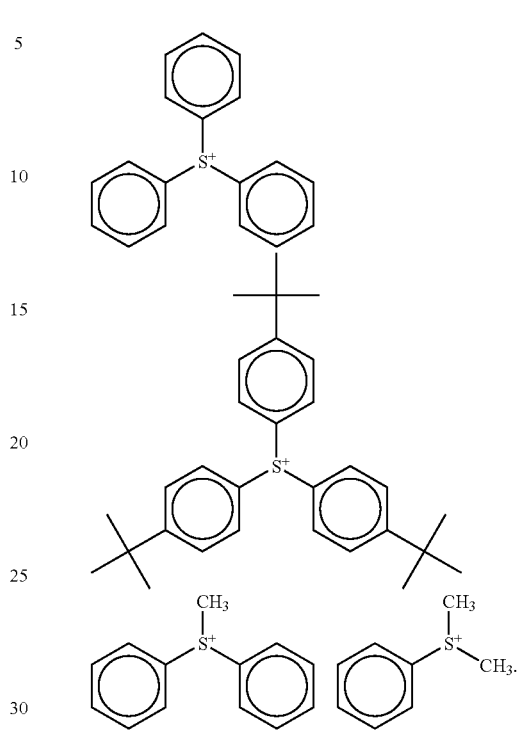

Mixtures of both $(X)_n-R-(SO_3^-)_m Z^{(n+m)+}$ and $R_6-SO_3^-Z^+$ photoacid generators are also contemplated herein.

The solvent for the antireflective coating is chosen such that it can dissolve all the solid components of the antireflective coating, and also can be removed during the bake step so that the resulting coating is not soluble in the coating solvent of the photoresist. Furthermore, to retain the integrity of the antireflective coating, the polymer of the antireflective coating, as well as the photoacid generator, is substantially insoluble in the solvent of the top photoresist. Such requirements prevent, or minimize, intermixing of the antireflecting coating layer with the photoresist layer. Typically propylene glycol monomethyl ether acetate and ethyl lactate are the preferred solvents for the top photoresist. Examples of suitable solvents for the antireflective coating composition are cyclohexanone, cyclopentanone, anisole, 2-heptanone, ethyl lactate, propylene glycol monomethyl ether, butyl acetate, gamma butyroacetate, ethyl cellosolve acetate, methyl cellosolve acetate, methyl 3-methoxypropionate, ethyl pyruvate, 2-methoxybutyl acetate, 2-methoxyethyl ether, but ethyl lactate, propylene glycol monomethyl ether acetate, propylene glycol monomethyl ether or mixtures thereof are preferred. Solvents with a lower degree of toxicity and good coating and solubility properties are generally preferred.

Typical antireflective coating compositions may comprise up to about 15 percent by weight of the solids, preferably less than 8 percent, based on the total weight of the coating composition. The solids may comprise from 0.01 to 25 weight percent of the photoacid generator, 50 to 99 weight percent of polymer, 1 to 50 weight percent of the crosslinking agent and optionally 0 to 25 weight percent of the acid or thermal acid generator, based on the total solids content of the antireflective coating composition. Preferably the photoacid generator level ranges from about 0.1 to about 20 weight %. Preferably the crosslinking agent ranges from about 5 to about 40 weight percent, more preferably 10 to 35 weight percent. The solid components are dissolved in the solvent, or mixtures of solvents, and filtered to remove impurities. The antireflective coating composition can optionally contain surfactants, base quencher, and other similar materials. The components of the antireflective coating may also be treated by techniques such as passing through an ion exchange column, filtration, and extraction process, to improve the quality of the product.

Other components may be added to the antireflective composition of the present application in order to enhance the performance of the coating, e.g. lower alcohols, dyes, surface leveling agents, adhesion promoters, antifoaming agents, etc. These additives may be present at up to 30 weight percent level. Other polymers, such as, novolaks, polyhydroxystyrene, polymethylmethacrylate and polyarylates, may be added to the composition, providing the performance is not negatively impacted. Preferably the amount of this polymer is kept below 50 weight % of the total solids of the composition, more preferably 35 weight %, and even more preferably below 20 weight %. Non-volatile bases may also be added to the composition to limit diffusion. Both non-volatile bases and non-volatile photodecomposable bases are known additives. Examples of non-volatile bases include ammonium hydroxide, tetrabutylammonium hydroxide, triethanolamine, diethanol amine, trioctylamine, n-octylamine, and trimethylsulfonium hydroxide. Examples of non-volatile photodecomposable bases include triphenylsulfonium hydroxide, bis(t-butylphenyl)iodonium cyclamate and tris(tert-butylphenyl) sulfonium cyclamate. Another component of the antireflective coating composition is a volatile amine, which is beneficial in enhancing the stability of the composition during storage and use. Suitable volatile amines are those which have a boiling point equal to or less than the solvent used in the antireflective coating composition. Examples of volatile amines include triethylamine, tributylamine, dibutylamine, diethylamine, monobutylamine, monoethylamine, aniline, substituted anilines, and the like, etc.

The absorption parameter (k) of the novel composition ranges from about 0.1 to about 1.0, preferably from about 0.15 to about 0.7 as measured using ellipsometry. The refractive index (n) of the antireflective coating is also optimized. The n and k values can be calculated using an ellipsometer, such as the J. A. Woollam WVASE VU-302™ Ellipsometer. The exact values of the optimum ranges for k and n are dependent on the exposure wavelength used and the type of application. Typically for 193 nm the preferred range for k is 0.1 to 0.75, for 248 nm the preferred range for k is 0.15 to 0.8, and for 365 nm the preferred range is from 0.1 to 0.8. The thickness of the antireflective coating is less than the thickness of the top photoresist. Preferably the film thickness of the antireflective coating is less than the value of (wavelength of exposure/refractive index), and more preferably it is less than the value of (wavelength of exposure/2 times refractive index), where the refractive index is that of the antireflective coating and can be measured with an ellipsometer. The optimum film thickness of the antireflective coating is determined by the exposure wavelength, refractive indices of the antireflective coating and of the photoresist, absorption characteristics of the top and bottom coatings, and optical characteristics of the substrate. Since the bottom antireflective coating must be removed by exposure and development steps, the optimum film thickness is determined by avoiding the optical nodes where no light absorption is present in the antireflective coating. For 193 nm a film thickness of less than 55 nm is preferred, for 248 nm a film thickness of less than 80 nm is preferred and for 365 nm a film thickness of less than 110 nm is preferred.

The antireflective coating composition is coated on the substrate using techniques well known to those skilled in the art, such as dipping, spin coating or spraying. Various substrates known in the art may be used, such as those that are planar, have topography or have holes. Examples of semiconductor substrates are crystalline and polycrystalline silicon, silicon dioxide, silicon (oxy)nitride, aluminum, aluminum/silicon alloys, and tungsten. In certain cases there can be a buildup of photoresist film at the edges of the substrate, referred to as edge bead. This edge bead can be removed using a solvent or mixture of solvents using techniques well known to those of ordinary skill in the art. The coating is then cured. The preferred range of temperature is from about 40° C. to about 240° C. for about 30-120 seconds on a hot plate or equivalent heating unit, more preferably from about 100° C. to about 200° C. for 45-90 seconds. The film thickness of the antireflective coating ranges from about 20 nm to about 300 nm. The optimum film thickness is determined, as is well known in the art, to be where good lithographic properties are obtained, especially where no standing waves are observed in the photoresist. The cured antireflective coating is also insoluble at this stage in the alkaline developing solution. The photoresist can then be coated on top of the antireflective coating.

Positive photoresists, which are developed with aqueous alkaline solutions, are useful for the present invention, provided the photoactive compounds in the photoresist and the antireflective coating absorb at the same exposure wavelength used for the imaging process for the photoresist. Positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the formation of a positive image in the photoresist coating. Photoresist resolution is defined as the smallest feature which the resist composition can transfer from the photomask to the substrate with a high degree of image edge acuity after exposure and development. In many manufacturing applications today, resist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the drive toward miniaturization reduces the critical dimensions on the devices.

Positive-acting photoresists comprising novolak resins and quinone-diazide compounds as photoactive compounds are well known in the art. Novolak resins are typically produced by condensing formaldehyde and one or more multi-substituted phenols, in the presence of an acid catalyst, such as oxalic acid. Photoactive compounds are generally obtained by reacting multihydroxyphenolic compounds with naphthoquinone diazide acids or their derivatives. The sensitivity of these types of resists typically ranges from about 300 nm to 440 nm.

Negative photoresists, which are developed with aqueous alkaline solutions, are useful for the present invention, provided the photoactive compounds in the photoresist and the antireflective coating absorb at the same exposure wavelength used for the imaging process of the photoresist. Negative-working photoresist compositions are exposed image-wise to radiation, those areas of the photoresist composition exposed to the radiation become more insoluble in the developer solution (e.g. a crosslinking reaction occurs) while those areas not exposed remain soluble in the developer solution. Thus, treatment of an exposed negative-working photoresist with the developer causes removal of the unexposed areas of the coating and the formation of a negative image in the photoresist coating. Photoresist resolution is defined as the smallest feature, which the photoresist composition can transfer from the photomask to the substrate with a high degree of image edge acuity after exposure and development. In many manufacturing applications today, photoresist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the drive toward miniaturization reduces the critical dimensions on the devices.

Negative-acting photoresists comprising novolak resins or polyhydroxystyrene, a crosslinking agent and quinone-diazide compounds as photoactive compounds are well known in the art. Novolak resins are typically produced by condensing formaldehyde and one or more multi-substituted phenols, in the presence of an acid catalyst, such as oxalic acid. Photoactive compounds are generally obtained by reacting multi-hydroxyphenolic compounds with naphthoquinone diazide acids or their derivatives. Oxime sulfonates have also been described as photoacid generators for negative photoresists as disclosed in U.S. Pat. No. 5,928,837, and incorporated by reference. The sensitivity of these types of resists typically ranges from about 300 nm to 440 nm.

Photoresists sensitive to short wavelengths, between about 180 nm and about 300 nm can also be used. Examples of such photoresists are given in the following patents and incorporated herein by reference, U.S. Pat. Nos. 4,491,628, 5,350,660, 5,069,997, EP 794458 and GB 2320718. Photoresists for 248 nm normally comprise polyhydroxystyrene or substituted polyhydroxystyrene derivatives, a photoactive compound, and optionally a solubility inhibitor. Particularly preferred for 193 nm and 157 nm exposure are photoresists comprising non-aromatic polymers, a photoacid generator, optionally a solubility inhibitor, and solvent. Photoresists sensitive at 193 nm that are known in the prior art are described in the following documents and incorporated herein, WO 97/33198, U.S. Pat. No. 5,585,219, Proc. SPIE, vols. 3333 (1998), 3678 (1999), 3999 (2000), 4345 (2001). Particularly preferred for 193 nm and 157 nm exposure are photoresists comprising non-aromatic polymers, a photoacid generator, optionally a solubility inhibitor, and solvent. Photoresists sensitive at 193 nm that are known in the prior art are described in the following references and incorporated herein, Proc. SPIE, vols. 3999 (2000), 4345 (2001), although any photoresist sensitive at 193 nm may be used on top of the antireflective composition herein.

An example of a negative photoresist comprises an alkali soluble fluorinated polymer, a photoactive compound and a crosslinking agent. The polymer has at least one unit of structure 1,

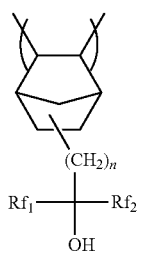

Where, $Rf_1$ and $Rf_2$ are independently a perfluorinated or partially fluorinated alkyl group; and n is 1-8. The negative photoresist composition comprises poly[5-(2-trifluoromethyl-1,1,1-trifluoro-2-hydroxypropyl)-2-norbornene], tetramethoxyglycoluril, triphenylsulfonium triflate and propylene glycol monomethyl ether acetate.

In positive systems, a film of photoresist is then coated on top of the cured antireflective coating and baked to substantially remove the photoresist solvent. The photoresist and the antireflective coating bilevel layers are then imagewise exposed to actinic radiation. In a subsequent heating step the acid generated during exposure step reacts to de-crosslink the polymer of the antireflective coating composition and thus rendering the exposed region of the antireflective coating alkali soluble in the developing solution. The temperature for the postexposure bake step can range from 40° C. to 200° C. for 30-200 seconds on a hot plate or equivalent heating system, preferably from 80° C. to 160° C. for 40-90 seconds. In some instances, it is possible to avoid the postexposure bake, since for certain chemistries, such as some acetal acid labile linkages, deprotection proceeds at room temperature. The polymer in the exposed regions of the antireflective coating is now soluble in an aqueous alkaline solution. The bilevel system is then developed with an aqueous alkaline developer to remove the photoresist and the antireflective coating. The developer is preferably an aqueous alkaline solution comprising, for example, tetramethyl ammonium hydroxide. The developer may further comprise additives, such as surfactants, polymers, isopropanol, ethanol, etc. The process of coating and imaging photoresist coatings and antireflective coatings is well known to those skilled in the art and is optimized for the specific type of photoresist and antireflective coating combination used. The imaged bilevel system can then be processed further as required by the manufacturing process of integrated circuits, for example metal deposition and etching.

In negative systems, a film of photoresist is then coated on top of the antireflective coating and baked to substantially remove the photoresist solvent. The photoresist and the antireflective coating bilevel system is then imagewise exposed. In a subsequent heating step the acid generated during exposure reacts to crosslink the polymer and thus render it alkali insoluble in the developing solution. In the unexposed regions the photoresist and the antireflective coating are soluble in the developing solution. The heating step may range in temperature from 110° C. to 170° C., preferably from 120° C. to 150° C. The bilevel system is then developed in an aqueous developer to remove the unexposed photoresist and the antireflective coating. The developer is preferably an aqueous alkaline solution comprising, for example, tetramethyl ammonium hydroxide. The developer may further comprise additives, such as surfactants, polymers, isopropanol, ethanol, etc. The process of coating and imaging photoresist coatings and antireflective coatings is well known to those skilled in the art and is optimized for the specific type of photoresist and antireflective coating combination used. The imaged bilevel system can then be processed further as required by the manufacturing process of integrated circuits, for example metal deposition and etching.

In a multilayer system, for example, a trilayer system, or process, the trilayer process is wear, for example, an organic film is formed on a substrate, an antireflection film is formed on the organic film, and a photoresist film is formed on the antireflection film. An organic film is formed on a substrate as a lower resist film by spin coating method etc. The organic film may or may not then crosslinked with heat or acid after application by spin coating method etc. On the organic film is formed the antireflection film, for example that which is disclosed herein, as an intermediate resist film. After applying the antireflection film composition to the organic film by spin-coating etc., an organic solvent is evaporated, and baking is carried out in order to promote crosslinking reaction to prevent the antireflection film from intermixing with an overlying photoresist film. After the antireflection film is formed, the photoresist film is formed thereon as an upper resist film. Spin coating method can be used for forming the photoresist film as with forming the antireflection film. After photoresist film composition is applied by spin-coating method etc., pre-baking is carried out. After that, a pattern circuit area is exposed, and post exposure baking (PEB) and development with a developer are carried out to obtain a resist pattern.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLE 1

Synthesis of bis(triphenylsulfonium) perfluorobutane-1,4-disulfonate

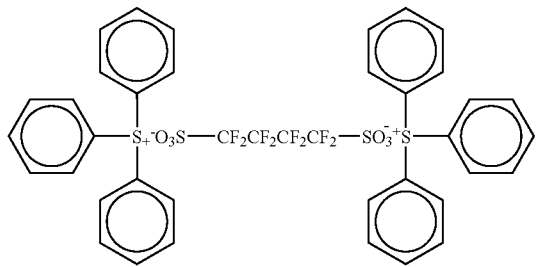

Perfluorobutane-1,4-disulfonic acid potassium salt (2.5 g) was added to a solution of triphenylsulfonium bromide (3.5 g) in 150 ml of water. Chloroform (150 ml) was added and stirred for 5 hours. The chloroform layer was washed several times with water, dried over anhydrous sodium sulfate, filtered, and the filtrate evaporated to an oil stage. Ether was added to the oil and the mixture was stirred vigorously. A white precipitate formed. The mixture was filtered and recovered precipitate was dried under vacuum, resulting in a white powder; mp 155° C.

EXAMPLE 2

Synthesis of bis(4-tert-butylphenyl)iodonium chloride

To a 2 L three necked flask (equipped with a mechanical stirrer, thermometer, addition funnel, and condenser/nitrogen inlet) was added 4-tert-butylbenzene (220 g, 1.64 moles), potassium iodate (100 g, 0.467 mole), methylene chloride (200 mL) and acidic anhydride (155 g 1.52 moles) under nitrogen and cooled to 5° C. Sulfuric acid was added slowly dropwise through the addition funnel while maintaining the temperature between 5 and 10° C. The reaction was then stirred at 5° C. for 5 hours and left overnight at room temperature. The reaction mixture was cooled again to 5° C. and maintained below 10° C. while 200 mL of water was added slowly dropwise. The resultant two phases were separated and the methylene chloride layer washed three times with 100 mL aliquots of distilled water. The washed organic phase was then stripped of solvents and dried under high vacuum to remove as much residual tert-butylbenzene as possible. The residue was then redissolved in 200 mL of methylene chloride and to this solution was added with stirring a solution of NaCl (27.3 g) in 200 mL of water. This two phase mixture was stirred overnight at 1000 rpm, separated and the organic layer washed 4 times with 100 mL of distilled water. The washed organic layer was stripped of stripped of solvent and the residue triturated with 200 mL of hexane three times to remove any remaining tert-butylbenzene. The final reside was broken up in ether and filtered to give 86 g of bis(4-tert-butylphenyl)iodonium chloride.

EXAMPLE 3

Synthesis of Silver Salt of Methanedisulfonate

Silver carbonate (20 g, 0.0725 moles) was added to methanedisulfonic acid (25.55 g 50% solution in water) and diluted in 25 mL of distilled water while stirring. The silver carbonate dissolved with effervescence of carbon dioxide. After the reaction was complete, any remaining insoluble material was removed by filtration and the filtrate was stripped of water was removed under vacuum to give 25.3 g of pure silver methanedisulfonate.

Using the above procedure with amount adjusted for stoichiometry, other silver salts were prepared using, as the acid, the following materials: 1,2-ethanedisulfonic acid, 1,3-propanedisulfonanic acid, cyclamic acid, 1S-10-camphorsulfonic acid and 1,3,5-benzenetrisulfonic acid (made from hydrolysis of 1,3,5-benzenetrisulfonyl chloride).

EXAMPLE 4

Synthesis of bis(triphenylsulfonium) methanedisulfonate

Silver methanedisulfonate (22 g, 0.0564 moles) from Example 3 was dissolved into 400 mL of acetonitrile. To this solution was added slowly with stirring a solution consisting of triphenylsulfonium bromide (38.74 g, 0.0113 moles) dissolved in 40 mL of distilled water. The reaction was stirred overnight and filtered to remove silver bromide. The filtrate was stripped of solvents. The resultant residue was crystallized three times by first dissolving the residue in a minimum of a hot mixture of chloroform and acetonitrile (~3/1) and then adding diethyl ether (~200 mL) to initiate crystallization. In this manner, 38 grams of pure bis(triphenylsulfonium) methanedisulfonate was recovered.

EXAMPLE 5

Synthesis of bis(tris(4-tert-butylphenyl)sulfonium) methanedisulfonate

Silver methanedisulfonate (1.74 g, 0.00447 moles) from Example 3 was dissolved into 3.5 mL of water. To this solution was added slowly with stirring a solution consisting of tris(4-tert-butylphenylsulfonium) iodide (5.00 g, 0.008951 moles) dissolved in 50 mL of acetonitrile. The reaction was stirred for 2 days and filtered to remove most of the silver iodide. The filtrate was then stripped of solvents, redissolved in a minimum of chloroform, and filtered through a 0.2 micron PTFE filter to remove residual solid. This filtrate was then crystallized with ether. This recrystallization was repeated two more times to give 2.30 g of pure product.

EXAMPLE 6

Synthesis of bis(bis(4-tert-butylphenyl)iodonium) methanedisulfonate

Following the procedure of Example 5, but using bis(4-tert-butylphenyliodionium)chloride in place of tris(4-tert-butylphenylsulfonium) iodide, bis(bis(4-tert-butylphenyl)iodonium) methanedisulfonate was made.

EXAMPLE 7

Synthesis of bis(tris(4-tert-butylphenyl)sulfonium)-1,2-ethanedisulfonate

Following the procedure of Example 5, but using silver 1,2-ethanedisulfonate in place of silver methanedisulfonate, bis(tris(4-tert-butylphenyl)sulfonium)-1,2-ethanedisulfonate was made.

EXAMPLE 8

Synthesis of bis(tris(4-tert-butylphenyl)sulfonium)-1,3-propanedisulfonate

Following the procedure of Example 5, but using silver 1,3-propanedisulfonate in place of silver methanedisulfonate, bis(tris(4-tert-butylphenyl)sulfonium)-1,3-propanedisulfonate was made.

EXAMPLE 9

Synthesis of tris(4-tert-butylphenyl)sulfonium cyclamate

Following the procedure of Example 5, but using silver cyclamate in place of silver methanedisulfonate, tris(4-tert-butylphenyl)sulfonium cyclamate was made.

EXAMPLE 10

Synthesis of tris(4-tert-butylphenyl)sulfonium camphorsulfonate

Following the procedure of Example 5, but using silver camphorsulfonate in place of silver methanedisulfonate, bis (tris(4-tert-butylphenyl)sulfonium) camphorsulfonate was made.

EXAMPLE 11

Synthesis of tris (tris(4-tert-butylphenyl)sulfonium)-1,3,5-benzenetrisulfonate

Following the procedure of Example 5, but using silver 1,3,5-benzenetrisulfonate in place of silver methanedisulfonate, bis(tris(4-tert-butylphenyl)sulfonium)-1,3,5-benzenetrisulfonate was made.

EXAMPLE 12

Synthesis of tris (bis(4-tert-butylphenyl)iodonium)-1,3,5-benzenetrisulfonate

Following the procedure of Example 5, but using bis(4-tert-butylphenyliodionium)chloride in place of tris(4-tert-butylphenylsulfonium) iodide and silver 1,3,5-benzenetrisulfonate in place of silver methanedisulfonate, tris (bis(4-tert-butylphenyl)iodonium)-1,3,5-benzenetrisulfonate was made.

EXAMPLE 13

Synthesis of bis(triphenylsulfonium)-1,3-propanedisulfonate

Following the procedure of Example 4, but using silver 1,3-propanedisulfonate in place of silver methanedisulfonate, bis (triphenylsulfonium)-1,3-propanedisulfonate was made.

EXAMPLE 14

Synthesis of Triphenylsulfonium Cyclamate

Following the procedure of Example 4, but using silver cyclamate in place of silver methanedisulfonate, triphenylsulfonium cyclamate was made.

EXAMPLE 15

Synthesis of Triphenylsulfonium Camphorsulfonate

Following the procedure of Example 4, but using silver camphorsulfonate in place of silver methanedisulfonate, triphenylsulfonium camphorsulfonate was made.

EXAMPLE 16

Synthesis of Monotriethylammonium Malonate

Malonic acid (10.4 g, 0.1 moles) was dissolved in 300 ml of ether at room temperature in a 3 neck 500 ml round bottom flask (the flask fitted with a stirrer) under dry nitrogen. Triethylamine (20.2 g, 0.2 moles) was dissolved in 50 ml ether at room temperature in a flask under dry nitrogen. The triethylamine solution was added to a 50 mL addition funnel under nitrogen and the addition funnel was then connected to the 500 ml round bottom flask. The amine solution was slowly added to the acid solution over a 5 minute period with stirring at a reaction temperature between 0 to −20° C. (by using a dry ice/acetone cooling bath). At the end of the reaction (stirring for at least 8 hours), the solvent was removed under vacuum using a Rotovap (the flask containing the material being stripped placed in a water bath at a temperature below 30° C.) for at least 16 hours until no more volatiles were removed, leaving a white solid material (17.80 g). Structure was confirmed by elemental analysis and $H^1$ NMR: Elemental Analysis (theoretical/found)-C (52.67/51.72); H (9.33/9.32); N (6.82/6.59); O (31.18/32.37)|$H^1$ NMR-1.2 ppm ($CH_3$ ethyl, 9H), 3 ppm ($CH_2$ ethyl and $CH_2$ malonate 8H).

Using the procedure in Example 16, the synthesis of monotriethylammonium malate, 1-butylmalonate, oxalate, glutarate, and succinate was done, replacing the malonic acid in the example with an equimolar quantity of the desired acid.

Structure was confirmed by elemental analysis and $H^1$ NMR: Elemental Analysis (theoretical/found): monotriethylammonium 1-butylmalonate-C (59.74/58.88); H (10.41/10.4); N (5.36/5.45); O (24.49/25.2)|H$^1$ NMR-0.8 ppm (CH$_3$ butyl), 3H), 1.2 ppm (CH$_3$ ethyl and CH$_2$—CH$_2$ butyl, 13H), 1.8 ppm (butyl CH$_2$-malonate, 2H), 3.1 ppm (CH$_2$ ethyl and CH malonate, 6H); monotriethylammonium oxalate-C (50.25/50.3); H (8.96/9.1); N (7.32/7.29); O (33.47/33.31)|H$^1$ NMR-1.38 ppm (CH$_3$ ethyl, 9H), 3.2 ppm (CH$_2$ ethyl, 6H); monotriethylammonium glutarate-C (52.57/53.68); H (10.03/9.25); N (5.57/4.67); O (31.83/32.4)|H$^1$ NMR-1.3 ppm (CH$_3$ ethyl, 9H), 1.9 ppm (CH$_2$, 2H), 2.4 ppm (CH$_2$CO$_2$, 4H), 3.05 ppm (CH$_2$ ethyl, 6H); monotriethylammonium succinate-C (54.78/53.01); H (10.03/9.25); N (5.57/4.67); O (31.83/32.4)|H$^1$ NMR-1.15 ppm (CH$_3$ ethyl, 9H), 2.45 ppm ((CH$_2$)$_2$ succinate, 4H), 3.05 ppm (CH ethyl, 6H); monotriethylammonium malate-C (51.05/50.61); H (9/8.98); N (5.95/5.38); O (34/35.03)|H$^1$ NMR-1.3 ppm (CH$_3$ ethyl, 9H), 2.7 ppm (CH$_2$ malate, 2H), 3.2 ppm (CH$_2$ ethyl, 6H), 4.2 ppm (CH malate, 1H).

EXAMPLE 17

Synthesis of poly(AdOMMA/EAdMA/α-GBLMA/AdMA/HAdA)

2-Ethyladamantyl methacrylate (EAdMA) (19.4 g), 2-hydroxyadamantantyl acrylate (HAdA) (22.78 g), α-gamma-butyrolactonyl methacrylate (α-GBLMA) (34.80 g), 2-adamantanyloxymethyl methacrylate (AdOMMA) (26.91 g), 1-adamantanyl methacrylate (AdMA) (11.28 g) and Perkadox-16 (5.44 g) were combined with THF (280 g) in a flask under nitrogen equipped with a reflux condenser and a mechanical stirrer. After purging with nitrogen while stirring, the reagents were heated with an oil bath to 70° C. The reaction mixture was stirred for 5 hours. After this time the polymer was precipitated into 2800 mL of methanol. The precipitate was air dried and dissolved into 400 mL of THF and precipitated again into 2800 mL of methanol. After recovering and drying the precipitate it was dissolved as above and precipitated twice into 2800 mL of hexane. The final polymer 95.6 g (83%) of white powder was recovered after drying in a vacuum oven overnight at 40° C.

EXAMPLE 18

Developable Bottom Antireflective Coating Composition

A solution of 1.842 g of poly(styrene-co-4-hydroxystyrene-co-tert-butylacrylate) (20/60/20), 197.2 g of PGME, 0.549 g of Vectomer 5015, 0.181 g triethylamine, 0.014 g bis(triphenylsulfonium)-1,4-perfluorobutanedisulfonate, 0.213 g monotriethylammonium malate (from Example 16) and 0.002 g R08 surfactant (Dainippon Ink & Chemicals) was prepared. The solution was mixed overnight and filtered through a 0.2 micron PTFE filter.

EXAMPLE 18A

Erosion Evaluation

The composition of Example 18 was repeated by substituting monotriethylammonium malate (Example 18A1), monotriethylammonium 1-butylmalonate (Example 18A2), monotriethylammonium oxalate (Example 18A3), monotriethylammonium glutarate (Example 18A4), and monotriethylammonium succinate (Example 18A5) for monotriethylammonium malate (in an equimolar amount).

Silicon wafers were coated with the composition of Example 18 as well as the compositions of this Example 18A. The wafers were prepared by spin coating the compositions onto a silicon wafer at a spin speed of ~2300 rpm and baked at 120° C. for 60 sec, forming a ~40 nm thick film. For each wafer, film thickness was measured before and after soaking in either AZ® EBR 70/30 or 2.38% tetramethylammonium hydroxide for 8 seconds. The data and results are shown in Table 2.

TABLE 2

| Example | EBR 70/30 | | | | TMAH | | | |
|---|---|---|---|---|---|---|---|---|
| | Initial FT | Final FT | Difference | % Change | Initial FT | Final FT | Difference | % Change |
| 18 | 393 | 393 | 0 | 0.00% | 392 | 391 | −1 | −0.26% |
| 18A1 | 392 | 393 | 1 | 0.26% | 391 | 390 | −1 | −0.26% |
| 18A2 | 385 | 386 | 1 | 0.26% | 384 | 383 | −1 | −0.26% |
| 18A3 | 400 | 397 | −3 | −0.75% | 399 | 398 | −1 | −0.25% |
| 18A4 | 389 | 371 | −18 | −4.63% | 389 | 387 | −2 | −0.51% |
| 18A5 | 391 | 373 | −18 | −4.60% | 390 | 388 | −2 | −0.51% |

EXAMPLE 19

Photoresist Composition

A solution of EAdMA/AdOMMA/HAdA/α-GBLMA/AdMA (from Example 17) (7.36 g), bis(4-tert-butylphenyl) iodonium bis-perfluoroethane sulfonimide, (0.22 g), bis (triphenylsulfonium) perfluorobutane-1,4-disulfonate (0.2 g), (bis(4-tert-butylphenyl)iodonium)-1,4-perfluorobutane-disulfonate (0.16 g), 2,6-disopropylaniline (0.04 g), FC 4430 (0.02 g), methyl-2-hydroxyisobutyrate (153.58 g), PGME (36.36 g), gamma-valerolactone (0.78 g) was prepared. This solution was rolled overnight, and then filtered through a 0.2 micron PTFE filter.

EXAMPLE 20

Lithographic Evaluation

A silicon substrate coated with the bottom antireflective coating composition of Example 18 (DBARC) was prepared by spin coating the bottom antireflective coating solution onto the silicon substrate at a spin speed of 2350 rpm and soft baked at 120° C. for 60 sec. The DBARC film thickness was 40 nm. The photoresist composition from Example 19 was then coated onto the DBARC coated silicon substrate. The spin speed was 1500 rpm and the photoresist film thickness was 150 nm and PAB of 100° C./60 seconds. The coated wafer was then exposed using a Nikon S306D 193 nm exposure tool using a NA=0.75 and conventional Illumination with a sigma of 0.6 s with a binary reticle). After exposure, the coated wafer was baked at a PEB of 115° C./60 s and developed in 2.38% TMAH at 21° C. for 30 seconds. Resolution down to 140 nm L/S feature (1:1 and 1:5 at same dose) was obtained with a dose of ~15-20 mJ/cm$^2$.

EXAMPLE 21

Developable Bottom Antireflective Coating Composition

Three developable bottom antireflective coating compositions were prepared as follows:
DBARC-A: AZ KrF-E01A, available from AZ Electronic Materials (Japan) K.K., Tokyo, Japan, was used as is.

DBARC-B: AZ KrF-E01A to which was added 5 wt % of triphenylsulfonium nonaflate.

DBARC-C: AZ KrF-E01A to which was added 5 wt % of bis (triphenylsulfonium) perfluorobutane-1,4-disulfonate from Example 1.

EXAMPLE 22

Lithographic Evaluation

Silicon substrates coated with the bottom antireflective coating compositions of Example 21 (DBARC) were prepared by first treating the silicon substrates with HMDS treated (120° C./35 sec) treated silicon wafers. Afterwards, DBARC-A, DBARC-B, and DBARC-C of Example 21 were applied to the HMDS treated silicon wafers at spin speed of 2500 rpm and soft baked at 180° C. for 60 sec. The film thickness of DBARC-A, DBARC-B, and DBARC-C were each 90 nm. A photoresist composition (AZ LExp. TCD-14, available from AZ Electronic Materials (Japan) K.K., Tokyo, Japan) was then spin coated onto the DBARC-A, DBARC-B, and DBARC-C coated substrates. The spin speed was 2500 rpm and the photoresist film thickness was 105 nm and a PAB of 120° C./90 seconds was used. The coated wafers were then exposed using a Canon FPA-3000 EX5 248 nm exposure tool using a NA=0.63 and ½ annular Illumination with a binary reticle. After exposure, the coated wafers were baked at a PEB of 130° C./90 s and developed in 2.38% TMAH at 23° C. for 60 seconds. Using these conditions, 200 nm L/S features, iso lines (220 nm) and trenches (220 nm) were obtained. From SEM, it was determined that the coated wafers using DBARC-A and DBARC-B showed residue of DBARC-A and DBARC-B, respectively, whereas the coated wafer using DBARC-C did not show any residue of DBARC-C.

Examples of negative bottom photoimageable antireflective coating compositions can be found in U.S. patent application Ser. No. 10/322,329, filed Dec. 18, 2002, the contents of which are hereby incorporated herein by reference.

In other systems, so that environmental demands of lower solvent emissions can be met, much of today's high solids and waterborne coatings are based upon low molecular weight resins and amino-formaldehyde crosslinkers. Conversion of these compositions into tough, chemically resistant, high performance films at reasonable cure temperatures requires the use of catalysts. Common backbone resins in these formulations include acrylics, alkyds, epoxies and polyesters. Typical amino crosslinking agents include melamines, ureas, glycolurils and benzoguanamines. Reaction of the backbone resin with an amino crosslinker can be greatly enhanced by the addition of the thermal acid compound of the present invention. While acid catalysts provide the fastest cure and lower curing temperatures, blocked catalysts are typically chosen for compositions requiring greater package stability. In addition, troublesome catalyst-pigment interaction is reduced or eliminated.

The foregoing description of the invention illustrates and describes the present invention. Additionally, the disclosure shows and describes only certain embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. An actinic radiation absorbing positive bottom photoimageable antireflective coating composition which is capable of being developed with an aqueous alkali developer and which is capable of being coated below a positive photoresist, wherein the antireflective coating composition comprises a polymer, a thermal acid generator, and a photoacid generator, where the photoacid generator is insoluble in a solvent of the photoresist, further where the photoacid generator is selected from a group consisting of
   (i) a photoacid generator where the cation is a monovalent cation with a volume of less than or equal to about 450 cubic angstroms, the anion is a divalent anion with a volume of less than or equal to about 205 cubic angstroms, and the photoacid generator has a melting point of at least 80° C.;
   (ii) a photoacid generator where the cation is a monovalent cation with a volume of less than or equal to about 450 cubic angstroms, the anion is a trivalent anion with a volume of less than or equal to about 220 cubic angstroms, and the photoacid generator has a melting point of at least 80° C.;
   (iii) a photoacid generator where the cation is a divalent cation with a volume of less than or equal to about 450 cubic angstroms, the anion is a monovalent anion with a volume of less than or equal to about 165 cubic angstroms, and the photoacid generator has a melting point of at least 130° C., and
   (iv) mixtures thereof.

2. A multilayer system comprising at least a first layer of claim 1, a second layer, and optionally, a third layer present under the first layer.

3. The composition of claim 1 wherein the photoacid generator is selected from the group bis(triphenylsulfonium) methanedisulfonate, bis-(triphenyl)sulfonium 1,3-propanedisulfonate, bis(triphenylsulfonium) perfluorobutanedisulfonate, tris bis(4-tert-butylphenyl)iodonium 1,3,5 -benzenetrisulfonate, tris tris(4-tertbutylphenyl)sulfonium-1,3,5-benzenetrisulfonate, bis-tris(4-tertbutylphenyl)sulfonium methanedisulfonate, bis -tris(4-tertbutylphenyl)sulfonium 1,2-ethanedisulfonate, bis-tris(4-tertbutylphenyl) sulfonium 1,3-propanedisulfonate, (thiodi-4,1-phenylene)bisdiphenylsulfonium nonaflate and mixtures thereof.

4. The composition of claim 1 which further comprises at least one volatile amine.

5. The composition of claim 1 wherein the polymer comprises at least one recurring unit with a hydroxyl and/or a carboxyl group and at least one recurring unit with an absorbing chromophore.

6. The composition of claim 5 where the absorbing chromophore is selected from compounds containing substituted aromatic hydrocarbon rings, unsubstituted aromatic hydrocarbon rings, substituted phenyl, unsubstituted phenyl, substituted anthracyl, unsubstituted anthracyl, substituted phenanthryl, unsubstituted phenanthryl, substituted naphthyl, unsubstituted naphthyl, substituted heterocyclic aromatic rings containing heteroatoms selected from oxygen, nitrogen and sulfur, unsubstituted heterocyclic aromatic rings containing heteroatoms selected from oxygen, nitrogen and sulfur, and combinations thereof.

7. The composition of claim 5 where the composition further comprises a dye.

8. The composition of claim 7, wherein the dye is selected from the group consisting of a monomeric dye, a polymeric dye and a mixture of a monomeric and a polymeric dye.

9. The composition of claim 5 where the polymer further comprises an acid labile group.

10. The composition of claim 9 where the acid labile group is selected from —(CO)O—R, —O—R, —O(CO)O—R, —C(CF$_3$)$_2$O—R, —C(CF$_3$)$_2$O(CO)O—R and —C(CF$_3$)$_2$(COOR), where R is selected from a group consisting of alkyl, substituted alkyl, cycloalkyl, substituted cycloalkyl, oxocyclohexyl, cyclic lactone, benzyl, substituted benzyl, alkoxy alkyl, acetoxy alkoxyoxy alkyl, tetrahydrofuranyl, methyl adamantyl, menthyl, tetrahydropyranyl and mevalonic lactone.

11. The composition of claim 1 which further comprises a vinyl ether terminated crosslinking agent.

12. The composition of claim 11 wherein the vinyl ether terminated crosslinking agent is R$^1$—(OCH=CH$_2$)$_n$ wherein, R$^1$ is selected from a group consisting of (C$_1$-C$_{30}$) linear alkyl, (C$_1$-C$_{30}$) branched alkyl, (C$_1$-C$_{30}$) cyclic alkyl, substituted (C$_6$-C$_{40}$) aryl, unsubstituted (C$_6$-C$_{40}$) aryl, substituted (C$_7$-C$_{40}$) alicyclic hydrocarbon and unsubstituted (C$_7$-C$_{40}$) alicyclic hydrocarbon; and n≧2.

13. The composition of claim 1, wherein the polymer comprises an absorbing chromophore group and a hydroxyl and/or a carboxyl group in the same recurring unit.

14. The composition of claim 1 where the thermal acid generator is a compound of formula (I)

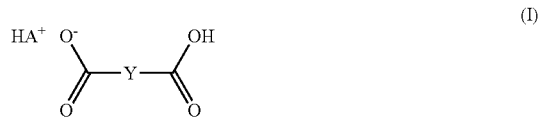

where Y is selected from a direct bond and a connecting group; and A is an unsubstituted or substituted amine compound.

15. A coated substrate comprising: a substrate having thereon; a layer of the antireflective coating composition of claim 1; and a layer of a positive photoresist composition above the antireflective coating composition.

16. A process for forming an image comprising: a) forming a coating of the bottom photoimageable antireflective coating composition of claim 1 on a substrate; b) baking the antireflective coating, c) providing a coating of a top photoresist layer over the antireflective coating; d) imagewise exposing the photoresist and antireflective coating layers to actinic radiation of same wavelength; e) post-exposure baking the photoresist and antireflective coating layers on the substrate; and, f) developing the photoresist and antireflective coating layers with an aqueous alkaline solution.

* * * * *